US012262697B2

(12) United States Patent
Schaefer et al.

(10) Patent No.: US 12,262,697 B2
(45) Date of Patent: Apr. 1, 2025

(54) APPARATUS AND METHODOLOGIES FOR IMPROVED DETECTION OF IMPORTANT BIOLOGICAL STATES IN ANIMALS

(71) Applicants: THE GOVERNORS OF THE UNIVERSITY OF ALBERTA, Edmonton (CA); Allan Schaefer, Lacombe (CA); Hartmut Von Gaza, Tofield (CA)

(72) Inventors: Allan Schaefer, Lacombe (CA); Hartmut Von Gaza, Tofield (CA); Clover Bench, Edmonton (CA); Hector Perez Marquez, Edmonton (CA)

(*) Notice: Subject to any disclaimer, the term of this patent is extended or adjusted under 35 U.S.C. 154(b) by 0 days.

(21) Appl. No.: 17/996,423

(22) PCT Filed: Apr. 16, 2021

(86) PCT No.: PCT/CA2021/050520
§ 371 (c)(1),
(2) Date: Oct. 17, 2022

(87) PCT Pub. No.: WO2021/207853
PCT Pub. Date: Oct. 21, 2021

(65) Prior Publication Data
US 2023/0225294 A1 Jul. 20, 2023

Related U.S. Application Data

(60) Provisional application No. 63/011,529, filed on Apr. 17, 2020.

(51) Int. Cl.
*A01K 29/00* (2006.01)
*G01J 5/00* (2022.01)
*G01J 5/48* (2022.01)

(52) U.S. Cl.
CPC .......... *A01K 29/005* (2013.01); *G01J 5/0025* (2013.01); *G01J 5/485* (2022.01); *G01J 2005/0077* (2013.01)

(58) Field of Classification Search
CPC ...... A01K 29/005; G01J 5/0025; G01J 5/485; G01J 2005/0077; A61B 2503/40; A61B 5/015; A61D 99/00
(Continued)

(56) References Cited

U.S. PATENT DOCUMENTS 5,474,085 A    12/1995 Hurnik et al.
6,974,373 B2*  12/2005 Kriesel .................. A22B 5/201
                                                        452/157
(Continued)

FOREIGN PATENT DOCUMENTS

WO      0057163 A1    9/2000
WO   2018143889 A1    8/2018

OTHER PUBLICATIONS

International Searching Authority, Indian Patent Office, International Search Report and Written Opinion for PCT/CA2021/05020, date mailed: Jun. 21, 2021, 10 pages.
(Continued)

*Primary Examiner* — Eric Blount
(74) *Attorney, Agent, or Firm* — Holzer Patel Drennan

(57) ABSTRACT

Embodiments herein are generally related to apparatus and methodologies for improved screening of important biological states in animals. The apparatus and methodologies comprise the use of high-resolution infrared thermography images collected about an animal to obtain both thermal information and behavioural information about the animal, wherein both thermal and behavioural information can be used to generate a comprehensive thermal prolife value that is indicative of the biologically important state in the animal.

14 Claims, 17 Drawing Sheets

(58) Field of Classification Search
USPC .................................................. 340/573.3
See application file for complete search history.

(56) References Cited

U.S. PATENT DOCUMENTS

| | | | |
|---|---|---|---|
| 7,277,744 | B2 | 10/2007 | Schaefer et al. |
| 9,565,837 | B2 | 2/2017 | Bench et al. |
| 9,955,672 | B2 | 5/2018 | Cook et al. |
| 10,964,019 | B2 * | 3/2021 | Spencer .................... G06T 7/70 |
| 2004/0154550 | A1 | 8/2004 | McQuilkin |
| 2015/0302241 | A1 * | 10/2015 | Eineren .................. G06V 40/10 |
| | | | 382/110 |
| 2019/0244350 | A1 | 8/2019 | Miodini et al. |
| 2022/0296158 | A1 * | 9/2022 | Steikuniene ......... A61B 5/0077 |

OTHER PUBLICATIONS

"Extended Search Report Issued In European Patent Application No. 21788121.8", Mailed Date: Mar. 18, 2024 8 Pages.

* cited by examiner (A)  (B)

| Day | Parameter | R value |
|---|---|---|
| Pull Day | Thermal Profile - 5 | 0.93 |
|  | Eye | 0.86 |
|  | Skin (Cheek) | 0.59 |
|  |  |  |
| Pull Day -1 | Thermal Profile - 5 | 0.74 |
|  | Eye | 0.58 |
|  | Skin (Cheek) | 0.56 |
|  |  |  |
| Pull Day -2 | Thermal Profile - 5 | 0.92 |
|  | Eye | 0.57 |
|  | Skin (Cheek) | 0.02 |
|  |  |  |
| Pull Day -3 | Thermal Profile - 5 | 0.84 |
|  | Eye | 0.51 |
|  | Skin | 0.14 |
|  |  |  |

*Figure 3*

FCE 3.2 ADG 795 RFI 551  
RIG -3.3 Tmean 34.2
FCE 1.7 ADG 1110 RFI -771  
RIG 5.3 Tmean 31.3
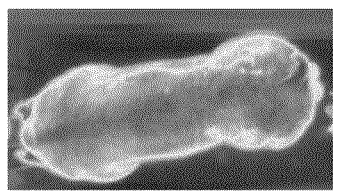 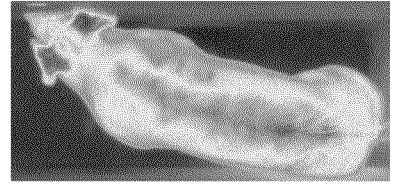 
Figure 4
FCE 3.2 ADG 795 RFI 551 RIG -3.3
FCE 1.7 ADG 1110 RFI -771 RIG 5.3
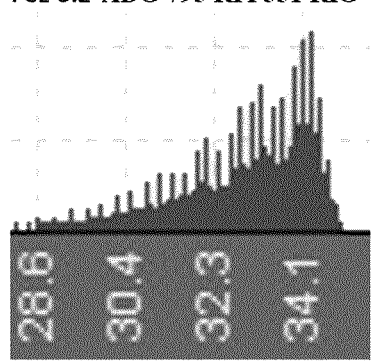 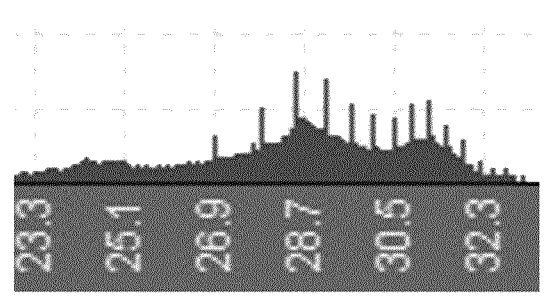
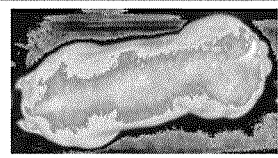 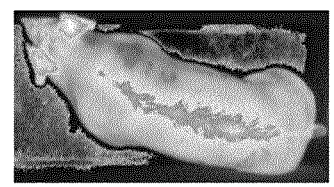
Figure 5

| Variable Y | RIG |
|---|---|
| Variable X | TSym |
| Sample size | 344 |
| Correlation coefficient r | -0.4075 |
| Significance level | P<0.0001 |
| 95% Confidence interval for r | -0.4921 to -0.3154 |

*Figure 6*

| Dependent Y | RIG |
|---|---|
| Weights | *** AutoWeight 1/SD^2 *** |

Weighted least squares multiple regression

| Method | Enter |
|---|---|

| Sample size | 344 |
|---|---|
| Coefficient of determination $R^2$ | 0.5038 |
| $R^2$-adjusted | 0.4995 |
| Multiple correlation coefficient | 0.7098 |
| Residual standard deviation | 1.3089 |

Regression Equation

| Independent variables | Coefficient | Std. Error | t | P | $r_{partial}$ | $r_{semipartial}$ |
|---|---|---|---|---|---|---|
| (Constant) | 2.9675 | | | | | |
| TEI | -10.4457 | 0.6121 | -17.064 | <0.0001 | -0.6792 | 0.6519 |
| TMean | 0.2370 | 0.04155 | 5.705 | <0.0001 | 0.2956 | 0.2179 |
| TSym | -0.6562 | 0.1651 | -3.974 | 0.0001 | -0.2107 | 0.1518 |

Analysis of Variance

| Source | DF | Sum of Squares | Mean Square |
|---|---|---|---|
| Regression | 3 | 591.5025 | 197.1675 |
| Residual | 340 | 582.4932 | 1.7132 |

| F-ratio | 115.0862 |
|---|---|
| Significance level | P<0.0001 |

*Figure 7*

| | |
|---|---:|
| Sample Size | 36 |
| Positive Group | 18 (50.00%) |
| Negative Group | 18 (50.00%) |
| Area under the ROC curve (AUC) | 0.806 |
| Standard Error | 0.0677 |
| 95% confidence interval | 0.640 to 0.918 |
| z statistic | 4.513 |
| Significance Level P (Area = 0.5) | <0.0001 |
| Youden Index J | 0.6111 |
| Sensitivity | 83.33 |
| Specificity | 77.78 |

|  | Block | | | | | Gestation | | |
|---|---|---|---|---|---|---|---|---|
| IRT Qarameter | A | B | C | D | P-value | 0 | 1 | 2 |
| TCP length | 20.12 | 49.64 | 29.54 | 25.03 | 0.01 | 27.46 | 24.87 | 33.12 |
| TCP Width | 12.23 | 34.33 | 17.43 | 14.32 | 0.01 | 16.64 | 14.26 | 17.92 |
| TCP area | 2949.06 | 912.59 | 2009.53 | 3413.91 | 0.24 | 1065.46 | 3382.90 | 2743.33 |
| IRT Rump | 30.95 | 31.34 | 32.87 | 31.96 | 0.01 | 31.06 | 31.77 | 31.50 |
| IRT Flank | 31.09 | 31.96 | 32.72 | 31.93 | 0.01 | 31.22 | 31.72 | 31.69 |
|  | Sample time | | | | | | | Parity |
|  | AM | Noon | PM | P-value | 1 | 2 | 3 | 4 |
| TCP length | 24.48 | 26.97 | 38.16 | 0.01 | 26.36 | 24.87 | 34.32 | 21.64 |
| TCP Width | 15.08 | 15.99 | 24.17 | 0.13 | 15.68 | 15.03 | 20.08 | 12.08 |
| TCP area | 2982.71 | 844.03 | 3538.02 | 0.01 | 1143.38 | 1618.19 | 1795.17 | 2899.11 |
| IRT Rump | 31.48 | 32.10 | 31.74 | 0.14 | 32.26 | 31.87 | 32.62 | 32.01 |
| IRT Flank | 31.66 | 31.98 | 32.12 | 0.31 | 31.83 | 32.04 | 32.58 | 31.39 |

*Figure 11*

| Table of Shape by Gestation |||||||
| Gestation |||||||
| Shape | 0 | 1 | 2 | 3 | 4 | Total |
|---|---|---|---|---|---|---|
| 1 | 3 | 0 | 3 | 0 | 9 | 15 |
|   | 2.5 | 0 | 2.5 | 0 | 7.5 | 12.5 |
| 2 | 3 | 15 | 7 | 5 | 9 | 39 |
|   | 2.5 | 12.5 | 5.83 | 4.17 | 7.5 | 32.5 |
| 3 | 3 | 4 | 5 | 5 | 0 | 17 |
|   | 2.5 | 3.33 | 4.17 | 4.17 | 0 | 14.17 |
| 4 | 5 | 3 | 4 | 4 | 3 | 19 |
|   | 4.17 | 2.5 | 3.33 | 3.33 | 2.5 | 15.83 |
| 5 | 0 | 0 | 1 | 2 | 0 | 3 |
|   | 0 | 0 | 0.83 | 1.67 | 0 | 2.5 |
| 6 | 10 | 2 | 4 | 8 | 3 | 27 |
|   | 8.33 | 1.67 | 3.33 | 6.67 | 2.5 | 22.5 |
| Total | 24 | 24 | 24 | 24 | 24 | 120 |
|   | 20 | 20 | 20 | 20 | 20 | 100 |

Figure 12A

| Table of Diffusion by Gestation |||||||
| Gestation |||||||
| Diffusion | 0 | 1 | 2 | 3 | 4 | Total |
|---|---|---|---|---|---|---|
| A | 3 | 1 | 3 | 0 | 8 | 15 |
|   | 2.5 | 0.83 | 2.5 | 0 | 6.67 | 12.5 |
| B | 5 | 14 | 9 | 9 | 10 | 47 |
|   | 4.17 | 11.67 | 7.5 | 7.5 | 8.33 | 39.17 |
| C | 16 | 9 | 12 | 15 | 6 | 58 |
|   | 13.33 | 7.5 | 10 | 12.5 | 5 | 48.33 |
| Total | 24 | 24 | 24 | 24 | 24 | 120 |
|   | 20 | 20 | 20 | 20 | 20 | 100 |

Figure 12B

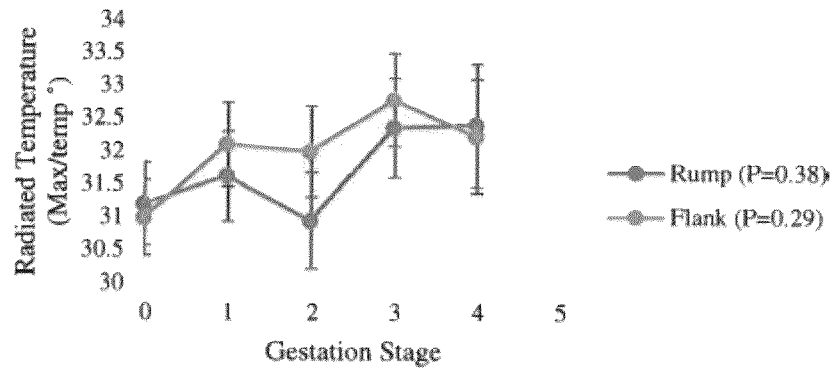
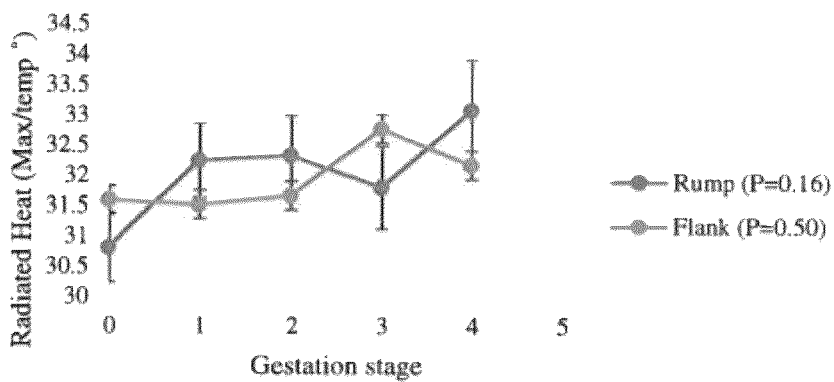
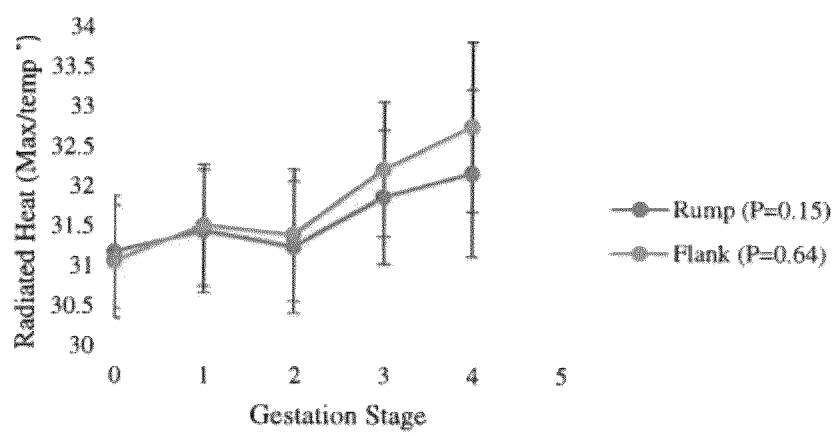
*Figure 12D*

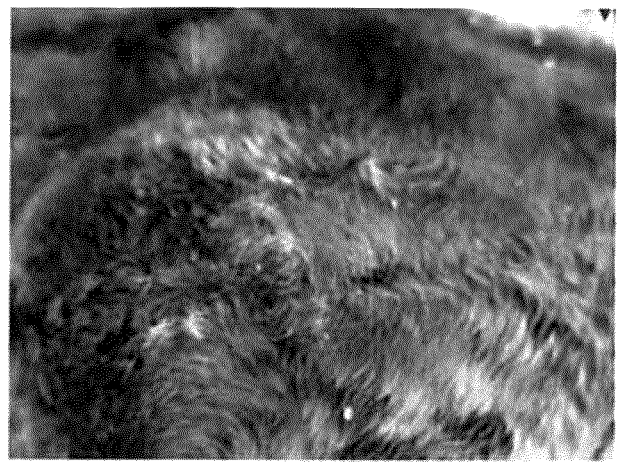
(A)
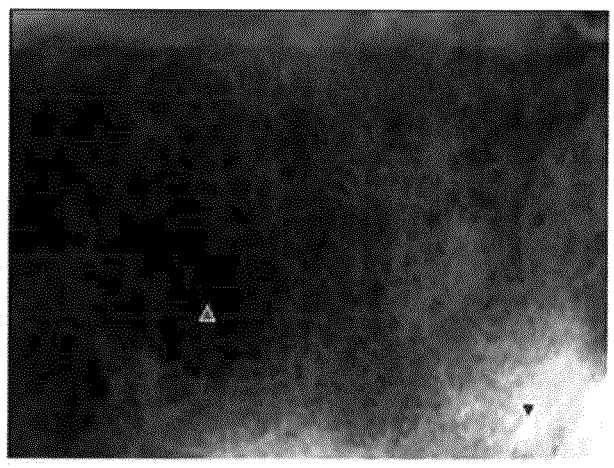
(B)
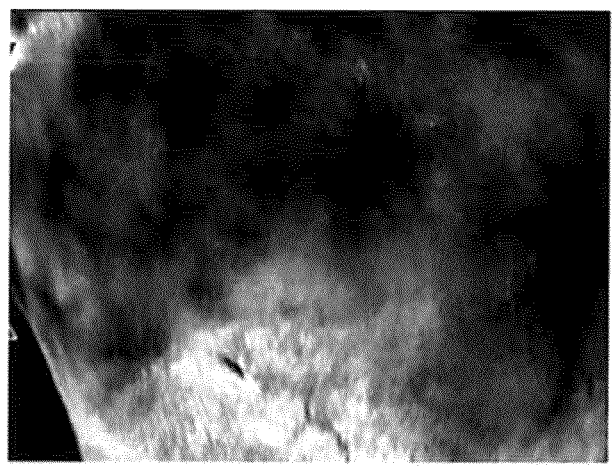
(C)
*Figure 14*

APPARATUS AND METHODOLOGIES FOR IMPROVED DETECTION OF IMPORTANT BIOLOGICAL STATES IN ANIMALS

CROSS-REFERENCE TO RELATED APPLICATIONS

This patent application claims the benefit of priority to U.S. Patent Application No. 63/011,529 filed Apr. 17, 2020, which is hereby incorporated by reference in its entirety.

FIELD

Embodiments herein are generally related to apparatus and methodologies for improved screening of important biological states in animals. More specifically, embodiments herein are directed to improved apparatus and methodologies for detecting comprehensive thermal profiles indicative of important biological states in animals.

BACKGROUND

There are many biological events in an animal's life that influence a plethora of biometric measurements and characteristics expressed. Some events are normal biological functions an animal will display, such as when they adapt to a changing environmental temperature, a changing growth period, or a changing endocrine event, such as puberty or estrus. The ability to detect, diagnose, and treat biologically important states in animals largely depends upon the effectiveness of the screening methods being used, and the timing that such methods are deployed. Early detection of biological states, such as disease, requires that reliable, comprehensive information about the animal's biological state be readily available early in the onset of the biological state.

By way of example, many animal management events experienced by livestock throughout the animal's lifetime can influence its overall welfare, performance (e.g. the quality of food it produces), and the cost of agricultural resources required. Exposure to handling and transport, co-mingling, auction, and time off-feed can cause stress in animals, impeding their immune system and increasing the incidence of disease. Left unmanaged, such events can have a considerable economic impact on the agricultural industry. The use of agricultural resources for the production of animal products is increasingly being scrutinized as human populations expand, increasing the need to mitigate carbon footprints and greenhouse gas emissions. Moreover, monitoring and controlling the impact animal management events can lead to improved animal welfare and quality, and to overall environmental benefits such as reduced carbon footprint and greenhouse gas emissions.

It is commonly recognized that effective animal management largely depends upon the ability to rapidly and non-invasively determine when animals are in steady or non-steady states (e.g. disease state, reproductive states, or growth phases) and, where applicable, to diagnose and treat such biologically important states as soon as possible. For example, respiratory disease in cattle can present the same challenges as in humans, where the animal can be well into the course of the disease before clinical scores or symptoms are observed. Animal caregivers are often left to decide whether blanket antibiotic treatment of all animals should be attempted, an ineffective approach against disease (and risking exacerbation of antibiotic resistance) and resulting in increased time and money. In contrast, if the caregiver could identify sick animals earlier and more effectively as True Positive (TP) or True Negative (TN), then a more targeted treatment and quarantine regime could be employed. Monitoring important biological states in animals is becoming increasingly important to the agricultural industry, as well as to zoo and wildlife biology settings because such states can influence a plethora of biometric measurements and characteristics (e.g., the animal's metabolic efficiency).

Unfortunately, traditional approaches of detecting clinical signs of an animal's biological state provide poor diagnostic results because observable signs often arise late into the course of the state (e.g., disease state, or illness). Traditional approaches, known as "pen-checking", are labour-intensive and subjective, requiring the on-site animal caregiver to observe the animal on a daily basis and to detect any abnormal behavioural patterns or clinical signs of illness (e.g. decrease in eating due to loss of appetite, etc.). Further, even if a disease state is recognized, it is often too late to halt the spread of infectious disease throughout a herd, or to prevent transmission to other herds or animal species (including humans).

More accurate approaches of detecting biological states in animals are known, such as the use of acute phase protein and/or hematology assessments. Although pen-checking can be combined with these more reliable approaches, the results can still be inaccurate as they require the capture and invasive, in vivo collection of biological samples from the animals. The requirement that the animal be captured and restrained itself causes stress, resulting in inaccuracies of the data collected. Moreover, the requirement that an animal caregiver be present for both pen-checking and sample collection not only increases the time and costs of the tests, but also further stresses the animals.

Attempts to improve the detection of biological states in animals have been made, such as through the use of non-invasive infrared thermography (IRT). IRT can be used to measure the dissipation of heat in animals and then to correlate the dissipation with specific disease states. Given that approximately ~60% of an animal's heat loss can occur in infrared ranges, IRT can be used as an early indicator of changes in an animal's biological state. Moreover, with the recent emergence of novel air-borne viruses, such as the coronavirus, and the resulting fever as a symptom of infection, there is marked increase in the need for effective thermal detection devices and methods of use.

Early examples of IRT being used to identify biological states, such as stress, in animals are known, where the stress is caused by, for example, transportation or other environmental factors. Unfortunately, early IRT methods are limited by only detecting heat loss due to stress or fever, leaving a need for more sophisticated methods of using infrared thermography to detect a broader range of important biological states (e.g. non-disease states).

Other early examples of IRT methods have attempted to study a broader range of biological states, including both veterinary and human medical applications. Such examples, however, are lacking in accuracy as they typically involve collecting thermal images, but then condensing the thermal data from the image into single or localized temperature information.

Adding to the foregoing limitations, animal caregivers are also inundated with a large variety of thermal detection devices at their disposal, without any guidance from specified industry standards, procedures, and protocols necessary for accurate data collection. Some devices are radiometric (quantitative), while others are not. Some devices have markedly different ranges of thermal resolutions and abilities, and are programmed for use on different anatomical areas across animals. Some devices are used to scan a crowd with spot detectors, with the devices being set to predetermined cut off values determined by the user's judgement/opinion (such devices also prone to technical errors, lack of accuracy and variable precision commonly arising from spot radiometers).

As a result, many IRT methods of collecting thermo-biometric information continue to be plagued by the use of low resolution (small number of pixels) devices and by the collection of only a single thermal value from one anatomical area, without any correction for environmental variation and without any standardization of the device or the body part being scanned. As confirmation, the restrictions of existing thermo-biometric methods have been well documented ("Thermometer guns on corona virus front lines are notoriously not accurate", The New York Times, Feb. 14, 2020).

For at least these reasons, there remains a need for improved non-invasive, early and accurate apparatus and methodologies of detecting, diagnosing, and treating biological states in animals. Some improved means of improving the reliability and accuracy of IRT methods of detecting and diagnosing biological states in animals has been to combine the IRT measurements with behavioural biometrics (e.g. micro behaviours, or clustering), as described in U.S. Pat. Nos. 9,565,837, 9,955,672, and 9,961,883. As IRT technology continues to advance, and as new, more complicated biological states arise in animals (e.g. novel viruses), the need for further improved apparatus and methodologies for accurate, reliable screening of biological states in animals remains.

SUMMARY

According to embodiments, a computer-implemented system for identifying at least one biological state in an animal is provided, the system comprising providing at least one high-resolution radiometric imaging device for obtaining infrared thermography images about the animal, the imaging device being operably connected to a processor, wherein the processor is programmed to receive the infrared thermography images and to analyse the images in order to obtain thermal information about the animal and to utilize the thermal information to calculate at least one thermal profile value, the thermal profile value being indicative of the at least one biological state in the animal. The at least one biological state may comprise a disease state, the animal's metabolic efficiency, and/or a reproductive state.

In some embodiments, the thermal information may comprise at least one of five factors. For example, the at least five factors comprise four thermal factors about the animal and one thermal factor about the animal's environment. In other embodiments, the thermal information may comprise at least one thermal coat pattern.

In some embodiments, wherein the processor may be further programmed to receive the infrared thermography images and to analyse the images obtain at least one form of behavioural information about the animal and to combine the behavioural information with the thermal information to generate the thermal profile value indicative of at least one biological state in an animal. The at least one behavioural information may comprise a kinematic expression or anatomical aspect about the animal.

According to embodiments, computer-implemented methods for identifying important biological states in an animal are provided, the methods comprising obtaining at least one infrared thermography images about an animal from a high-resolution radiometric imaging device and processing the at least one infrared thermography image about the animal to obtain thermal information about the animal, wherein the thermal information can be used to calculate a thermal profile value, the thermal profile value being indicative of the at least one biological state in the animal. The at least one biological state may be selected from the group consisting of a disease state, metabolic efficiency, and a reproductive state.

In some embodiments, the thermal information comprises at least one of five factors. For example, the at least five factors comprise four thermal factors about the animal and one thermal factor about the animal's environment. In other embodiments, the thermal information comprises at least one thermal coat pattern.

In some embodiments, the present methods may further comprise obtaining at least one behavioural information about the animal from the infrared thermography images, and combining the behavioural information with the thermal information to generate the thermal profile value, the thermal profile value being indicative of at least one biological state in an animal. For example, the behavioural information may comprise a kinematic expression or anatomical aspect about the animal.

BRIEF DESCRIPTION OF THE DRAWINGS

FIG. 3 shows the correlation between the thermal profile values shown in FIG. 2, and a corresponding single test anatomical site for True Positive (TP) animals;

FIG. 4 shows infrared thermographic images of an animal, wherein a thermal profile pattern generated from the images determined an animal to have an inefficient metabolic efficiency (left) and an efficient metabolic efficiency (right), according to embodiments;

FIG. 5 shows thermal histogram data depicting the number of pixels contained in thermal histogram bins for the animals shown in FIG. 4, i.e. the animal having inefficient metabolic efficiency (left) and the animal having efficient metabolic efficiency (right), according to embodiments;

FIG. 6 shows the results of the relationship between the thermal symmetry (TSym) determined for the thermal histogram bins shown in FIG. 5 as compared to convention residual intake and gain (RIG), according to embodiments;

FIG. 7 shows the contribution of the thermal symmetry (TSym) value shown in FIG. 6 to the regression equation defining the correlation between metabolic efficiency (RIG) and thermal symmetry (TSym), according to embodiments;

FIG. 8 shows example thermal coat patterns (TCPs) detected according to embodiments herein, the TCPs being detected when an animal has a biologically important state (i.e. pregnancy.

FIG. 11 provides the results of a pixel and infrared thermography analysis (LSMeans and P-values) from the generalize linear mix model (model=sample day/Block/Parity and Gestation with Cow as random effect);

FIG. 14 provides example images of the presently obtained infrared thermography images, such images being analyzed to determine the spread of TCPs of the animals, according to embodiments;

DETAILED DESCRIPTION OF THE PREFERRED EMBODIMENTS

Figure 1:
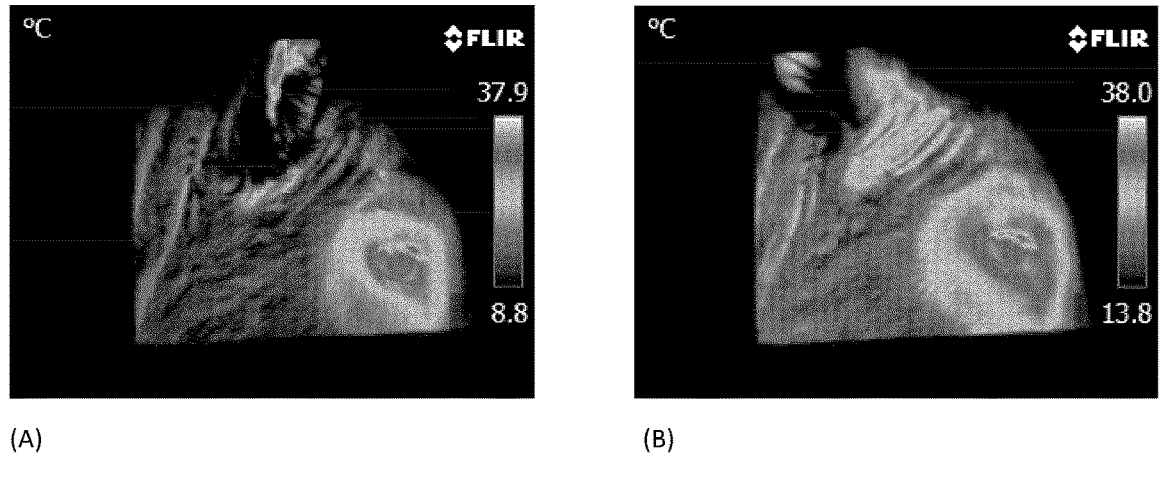
FIG. 1 shows infrared thermographic images of an animal, wherein a thermal profile value generated from the images determined the animal to be in a True Negative (TN) biologically important state (A), and then in a True Positive (TP) biologically important state (B), the images being from the same animal.

According to embodiments, apparatus and methodologies are disclosed for high-resolution, non-invasive radiometric imaging of animals, such imaging providing and reliable means for generating a comprehensive thermal profile about the animal, the thermal profile for detecting, diagnosing, and treating important biological states in animals. Herein, the described apparatus and methodologies may provide for the use of thermal information and/or behavioural information, such information simultaneously obtained about an animal via at least one infrared thermography image, and operative to generate at least one thermal profile about the animal that indicates an important biological state about the animal.

Broadly, the term "biological state" of an animal means any physiological condition, steady or non-steady state, febrile and/or disease states, including diseases caused by virus, bacteria, fungus, yeast, micro-toxins, and the like, such as respiratory disease states caused by a complex pathogen primarily triggered by a viral infection (e.g. without limitation, corona virus) including, without limitation, respiratory disease states in respiratory tract (e.g. without limitation, upper respiratory tract), reproductive state, including estrus and/or ovulation, and/or growth phase, including metabolic efficiency. Although some biologically important disease states are described herein, such biological states are provided for illustration purposes only.

It is contemplated that the present apparatus and methodologies may be used to detect, diagnose, and treat other biologically important states, as may be appreciated in the art. It should be understood that the term biological state may also include any agriculturally important states, and may be determined in an individual animal or it a population of group-housed animals.

It should be understood that the presently described biological states may be detected, diagnosed, and treated with or without considering other environmental factors such as air temperature (thermal neutral zones), humidity, or other such factors as may impact the biological states, etc. That is, the present apparatus and methodologies may be used to detect biological states in animals by measuring temperature changes that may occur due to the environment, steady-state changes (e.g. growth curves), and non-steady states that can be driven by immune challenges and/or disease.

It should be understood that the presently described apparatus and methodologies may provide means for detecting, diagnosing, and treating biological states in animals comprising providing a system operative to automatically capture a recording of images about an animal, as identified by animal identification means (e.g. RFID tags), whether the animal is alone or in a group of penned animals.

According to embodiments, the present apparatus and methodologies comprise the use of at least one high-resolution imaging device for simultaneously capturing both temperature and behavioural information about an animal. In some embodiments, the apparatus may comprise a device for capturing and measuring a plurality infrared thermography images about the animal, i.e. electromagnetic radiation or radiometric measurements, otherwise explained as the intensity of thermal radiation emitted by the animal. In some embodiments, the apparatus may comprise a device for also capturing and measuring a plurality of behavioural measurements about the animal.

Without limitation, one example of the present imaging device may comprise a broad-spectrum infrared thermography camera, such as a FLIR ThermaCAM S60 high resolution camera (e.g. 320×240-pixel, uncooled microbolometer FBA detector technology), with a thermal sensitivity of <0.04° C. at 30° C. and accuracy of ±2%. The present imaging device may also comprise a FLIR ThermaCAM A65 or A35, or other such commercially available devices having a resolution of at least 640×512 or 320×250, respectively. Such imaging devices may comprise a powerful, real-time data acquisition system featuring highly sensitive thermal imaging, precision temperature measurement and extensive data analysis capabilities, providing the capture of high resolution, longwave images with over 76,000 picture elements.

The plurality of images may be captured automatically, in real-time. The plurality of images may be captured continuously, as a video (e.g. a video clip of seconds or minutes). In some embodiments, the plurality of images may be captured automatically, via motion sensors activated by the presence of an animal, and may be connected to an Ethernet switch located at the central hub via an Ethernet connection. For example, the present system may include at least one motion detector for detecting motion in the area at, near or around the imaging devices in the event of an animal approaching or present at the devices. As will be appreciated, in addition to the detection of an animal approaching or being present at the at least one device, identification of the animal, and both thermal and behavioural information about the animal can be captured. In some embodiments, the present system may further comprise one or more sensors to continuously monitor environmental parameters in the area including, without limitation, humidity, temperature, and moisture in the area.

In other embodiments, it is contemplated that the apparatus may comprise a device for capturing and measuring a plurality of multispectral images (MSI), while in other embodiments, the apparatus may comprise a device for capturing and measuring kinematic expression and/or anatomical (facial) aspect images. For example, in some embodiments, the present system may comprise a visual or laser point cloud device for use with the presently described imaging devices.

In some embodiments, the plurality of images may be captured by a plurality of imaging devices, such devices positioned at various areas throughout an animal enclosure. Each imaging device may be operably connected to a central processor for receiving the images from the devices and for integrating the information therefrom for analysis thereof (as will be described in more detail below).

Herein, the at least one imaging device may be operably connected to corresponding equipment and computer software, such that the images can be automatically transferred, uploaded, or received by a central processor. In some embodiments, the imaging devices may be adapted to communicate with the central processor over a wired network, wherein the imaging information may be collected locally via the processor and sent to a hosted database related to the processor over a wired network for viewing and/or analysis. In other embodiments, the at least one imaging devices may be adapted to communicate with the processor over a wireless network via a communication component for remote viewing and/or analysis.

The at least one imaging device may be positioned at or near a location where at least one animal is present. For example, the at least one imaging device may be positioned at or near an animal pasture, an enclosure including gestation, nursery, and commercial barns, or the like. In some embodiments, the enclosure may comprise, without limitation, a water or food station, trough or automated feeders. The at least one imaging device may be removably or permanently mounted at or near the enclosure. As would be understood by one skilled in the art, an enclosure may comprise any area or structure which accomplishes the desired functions herein, including providing for the positioning of the at least one imaging devices near an animal without having to restrain or reduce the animal's movement.

In other embodiments, the at least one imaging device may be suspended above the animal, such as by an unmanned aircraft, a flying robot, a drone, or other software-controlled airborne device. In yet other embodiments, the at least one imaging device may comprise a hand-held device. Without limitation, the at least one imaging device may be positioned in any manner so has to accurately obtain at least thermal and behavioural information about the animal as accomplished herein, and specifically without disturbing the animal (i.e. without the animal being aware of such information being collected).

In some embodiments, the at least one imaging device may be operative to automatically collect at least one time-stamped image, such image being triggered by the presence of the animal at or near the imaging device. Each time-stamped image may be classified as a "behavioural event" and may be further analyzed to generate a behavioural profile about the animal (as will be described in more detail below).

According to embodiments, the present apparatus and methodologies may provide for the capture of at least one form of behavioural information about the animal (e.g. bio-mechanical features), the behavioural information being collected and analyzed to generate a behavioural profile about the animal. In some embodiments, the behavioural profile may be indicative of at least one biologically important state in an animal, whether the behavioural profile is considered alone or in combination with at least one thermal profile.

According to embodiments, the present apparatus and methodologies may provide means for detecting changes in thermal topography of an image, e.g. a face (ear), a flank, or a rump (tail) of an animal. The present apparatus and methodologies may further provide means for obtaining a thermal profile that corresponds with the topography, e.g. tail movement or tail arc, "tail wobble", and/or ear placement/angle. In some embodiments, the presently obtained at least one form of behavioural information may correspond with at least one thermal profile. For example, as will be described herein, a thermal pattern about an animal may demonstrate a particular temperature profile (e.g. temperature differences at the rump of the animal), said profile correlating with a behaviour (e.g. placement of the tail at the rump).

That is, for example, it may be shown that where a temperature change is observed as a decrease at the animal's rump, said temperature decrease may be correlated with the animal's tail being placed directly downwardly (i.e. the tail is positioned straight down). Alternatively, it may be shown that where a temperature change is observed as a decrease at the animal's face, said temperature decrease may be correlated with the animal's ears being positioned rearwardly (i.e. the animal's ears may be pushed back). As might be appreciated by those skilled in the art, if the presently defined images are obtained from different profiles of the animal, there will be different landmarks in relation (e.g. where the profile is of the head of the animal, the landmark may differ if the ears are observed to droop or be pushed backwards).

As will be described in more detail, the present apparatus and methodologies may comprise biometric-based means for analyzing bio-mechanical features of an animal. In some embodiments, the apparatus and methodologies may comprise the use of quantified algorithms and image analysis to track reflective markers using an optical motion system. Biometric techniques that include three-dimensional fields (e.g. X, Y, and Z) have been successfully used to analyze movements precisely to identify biomechanical abnormalities and gait in animal science. For example, it has been shown that 3D-kinematics can also be used to identify micro-lordosis movements in animals (e.g. small pelvic side-to-side and front and back movements), such movements occurring during a 24-hour period prior to ovulation. Other information, such as posture angles, complement these types of bio-mechanical data by analysing the articulation of movements via spatial reference axes for proximal and distal body segments to measure behaviour biometrics that can be used for diagnostic purposes (e.g. detection of biologically important states in animals) in livestock production.

Accordingly, in some embodiments, the present apparatus and methodologies may comprise means for collecting and analyzing biometric-based information about an animal, such information being indicative of at least one biologically important state in an animal. For example, without limitation, the present apparatus and methodologies may comprise means for at least one thermal image about an animal, such image operative for obtaining and characterizing movement biomechanics triggered by postural (angle) changes in the animal. For example, the presently described 3D kinematics may be operative to detect subtle changes in postural angles associated with, without limitation, pelvic tilt, lateral pelvic shifts (left and right), foot strikes (left and right), and tail movements at different sizes (macro, mid, and micro). In some embodiments, the present apparatus and methodologies may serve to optimize characterization of the behaviour profiles by identifying optimum reference values based on the frequency of these changes in postural angles during the detection of the biological state that can be used to differentiate between different biological states such as, for example, the estrus period, proestrus, and ovulation days in naturally cycling cows. That is, as will be shown, for example, the presently collected behaviour biometric information about an animal may change, such change reflecting the onset of a biological state in an animal (e.g. changes occurring as ovulation approaches during the estimated estrus period compared to the proestrus (baseline) period).

According to embodiments, the present apparatus and methodologies may provide for the processing and analysis of the at least one infrared thermography image about the animal to generate at least one comprehensive thermal pattern reflective of at least one important biological state in the animal.

Broadly, the term "thermal pattern" of an animal means comprehensive thermal or temperature information determined about an animal, the thermal information being obtained from at least one infrared thermography image. In some embodiments, the thermal information may comprise a plurality of factors that may be used to generate an overall thermal pattern including, without limitation, maximum temperature (TMax) of a first area (e.g. eye), average temperature (Mean ° C.) about at least one second area (e.g. cheek), differences therebetween (e.g. Δ° C. of TMax and Mean ° C.), normalization of environmental effect (e.g. regression of what the expected temperature might be and what temperature is actually detected), and thermal topography (which can be used in combination with the temperature and/or pre-clinical symptoms expressed prior to the illness being observed), thermal patterns, thermal symmetry or asymmetry and fluctuations (e.g. increase and decreases).

In some embodiments, the term "thermal pattern" of an animal means comprehensive thermal or temperature information determined about an animal, the thermal information being obtained from at least one infrared thermography image including, without limitation, infrared thermography information collected and/or measured on the skin of the animal in order to detect a thermal coat pattern or 'TCP'. For example, the thermal pattern may comprise performing an image analysis of the at least one infrared image to compare the size, shape, and occurrence of thermal patterns (e.g. a TCP). That is, in some embodiments, the thermal pattern may comprise processing said images about an animal by measuring the number or amount of pixels inside the TCP and the length and width of the TCP using a predetermined region of interest. In some embodiments, measuring the number or amount of pixels inside the TCP may comprise scanning the image and determining a representative portion of the image (i.e. graphically selecting a geometrical portion of the image based upon the optimized or best representation of the thermal profile). The processed information can then be used to rank the data and selecting a representative image (e.g. the largest TCP), and utilizing the largest TCP selected for analysis of the thermal pattern. In addition, in some embodiments, the thermal pattern may comprise performing a photographic scale analysis of the at least one infrared image, such scale analysis performed by calculating the frequency (e.g. Proc Freq in SAS 9.4) of shape and diffusion for each stage of biological state.

As will described, the presently generated thermal patterns are significantly more efficient and effective at determining and/or detecting at least one biological state in an animal, and specifically more efficient and effective than merely utilizing a single thermal pixel temperature point (as commonly used with hand held thermal radiometers). Herein, it is contemplated that one or more testing approaches may be used in conjunction with, or parallel to, the present apparatus and methodologies, whether the one or more testing approach is introduced at the screening stage, increasing testing sensitivity, and making it less like that a true positive is missed, or otherwise.

According to embodiments, the present apparatus and methodologies may further comprise at least one animal identification means, such that a plurality of images taken about different animals can be distinguished (e.g. ear tags, paint or other markings, implanted tags, or the like). In some embodiments, the present system may comprise at least one radio frequency identification (RFID) transponder and a sensor coupled thereto for detecting at least one unique digital identification tag (e.g. RFID tag). In such embodiments, the system may further comprise at least one RFID reader, such as a panel reader (Alflex EID System) capable of transmitting radio frequency signals and reading said signals. Tag information from such panels may be communicated to an Ethernet converter (B&B Electronics), which may multiplex the signal from the readers and connected to one of the ports on the Ethernet switch.

Herein, the at least one animal identification means may be positioned at or near the at least one imaging device, and may be operative to transmit animal identification information about the animal to the central processor for processing (e.g. ear tags, radio-frequency identification (RFID) tags, paint or other markings, implanted tags, or the like). In some embodiments, the animal identification means may comprise radio frequency identification (RFID) transponder, such that each RFID tag on an animal identification means may be positioned at or near the at least one imaging device.

According to embodiments, the present apparatus and methodologies may provide for the plurality of images to the transmitted to for processing by at least one central processor. The central processor may be adapted to perform various types of image processing algorithms and/or various modes of operation (including to process and store recorded video images). The central processor may comprise a central processing unit (CPU) or the like, having a power component and a memory component, and be operatively connected to the at least one thermal imaging device. In some embodiments, the process may comprise a display component for displaying the information indicative of one or more important biological state about an animal. The processor controls, for example, the at least one thermal imaging devices to acquire the infrared thermography images therefrom, the images processed by the processor to obtain both thermal information and behavioural information about an animal. Then, based upon the obtained thermal and/or behavioural information, the processor is operative to generate a thermal profile about the animal, said thermal profile indicative of at least one biologically important state in the animal.

In some embodiments, it should be appreciated that the central processor may be integrated in software and/or hardware as part of a processing component or code (e.g., software or configuration data) for each mode of operation and for analysing a plurality of infrared thermography images, which may be stored in a memory component or a general information database. The information from the plurality of images may be stored by a separate computer-readable medium (e.g., a memory, such as a hard drive, a compact disk, a digital video disk, or a flash memory) to be executed by a computer (e.g., logic or processor-based system) to perform various methods disclosed herein.

In some embodiments, the at least one central processor may be remotely monitored and controlled, such as via an internet connection or other network paradigms operative to collect, transmit, and/or receive information. The processor may be programmed to run any relevant internet-based program, and may be operative to process live video of thermal images and current temperature data. The system may be remotely controlled, including management of the thermal images via the camera position, angle, focus and emissivity. Without limitation, the central processor may comprise any form of device operative to transmit or receive information via wired or wireless signaling, via a plurality of user interfaces (e.g. desktop computers, notebook computers, laptop computers, mobile devices such as cellphones and tablets), via cloud computing, via application program interfaces ("API"), or the like.

In some embodiments, the processor may be operatively and electronically connected to at least one general information database, the database containing historical data about the animals and/or any other relevant information as may be known in the art (e.g. any information as may be used for predictive thermal profile calculations, as will be described herein).

In some embodiments, the at least one central processor may be operative to simultaneously and continuously generate at least one thermal profile about an animal and to update the general information database according to feedback and machine learning systems, such updating further incorporating information from the general information database and updating said information. The central processor may perform one or more different modes of operation including the detection and analysis of thermal information about an animal, the detection and analysis of behavioural information about an animal, or both, the modes of operation being predetermined and/or selected to determine a plurality of important biological states in an animal.

Herein, although the present disclosure generally relates to cows and pigs, it should be understood that the present apparatus and methodologies may be utilized to detect, diagnose and treat biological states in any animal including, without limitation, humans, domestic ruminant and monogastric animals, such as livestock, including cattle, horses, domestic ungulates and fowl.

Analysis:

The present apparatus and methodologies will now be illustrated in more detail by way of the following Examples.

EXAMPLES

Example 1: This Example demonstrates the use of the present apparatus and methodologies for the detection, diagnosis, and treatment of biological states in animals, wherein the biological state comprises at least one disease, such as a respiratory disease. As will be described, a comprehensive thermal pattern about the animal is generated, said thermal pattern indicative of at least one biologically important state in the animal.

As above, it is imperative that respiratory disease due to viral infection in animals be treated. For example, respiratory diseases are one of the most important diseases in cattle, such diseases being caused by a complex of pathogens primarily triggered by virus infection including bovine coronavirus (BCV), bovine viral diarrhea virus (BVDV), bovine respiratory syncytial virus (BRSV), bovine herpesvirus type 1 (BHV-1) and bovine parainfluenza virus type 3 (BPIV3). Unfortunately, by the time clinical scores (symptoms) are observed, the animal is well into the course of the disease, and animal caregivers must grapple with the tactical decision of whether to treat all animals with antibiotics, a strategy that is not effective for virus disease control and moreover is expensive and exacerbates antibiotic resistance. The challenge with an animal model is the same as in humans.

Apparatus and methodologies for earlier and more effective detection, diagnosis of true positive (TP) or true negative (TN) animals suffering from a biologically important states, such as respiratory disease, are needed.

According to embodiments, apparatus and methods for identifying important biological states in an animal are provided, the biological state comprising a disease state (e.g. a respiratory disease state). In addition to the presently described apparatus and methodologies, by way of control data, clinical scores and corresponding laboratory tests (e.g. serology, hematology, cortisol, and core body temperature) were also performed and the data analysed.

In this Example, fourteen (14) multiple sourced, comingled and recently transported commercial beef calves (average 220 kg) were brought in as a group to the beef cattle animal unit at the Agriculture and Agri-Food Canada facility in Lacombe, Alberta, Canada.

At least one automated broad-spectrum infrared thermography (IRT) imaging device (e.g. FLIR S60 high resolution camera (320×240 pixels)) was positioned at or near the animal's water station. Each at least one imaging devices captured a plurality of images daily, several times per day, as the animals attended the water station, the device being triggered automatically by the presence of one or more animals entering the water station.

For example, the at least one imaging devices may themselves comprise and/or may be operatively connected to a motion sensor adapted to activate the imaging device automatically capture a plurality of images, said images being obtained about the area generally, the animal, and/or a combination thereof. The images may then be transmitted to one or more processors for analysis (as will be described), and to one or more databases for storing the images in a memory component for further analysis. As will be appreciated, the plurality of images obtained by the at least one imaging devices may comprise at least thermal information about the animal, behavioural information about the animal, or a combination thereof.

Each of the plurality of images were received by the at least one imaging device at a central processor, the processor programmed according to a mode of operation to generate at least one comprehensive thermal pattern or thermal profile value (TPV) about each animal, the TPV being indicative of the animal's biological state (i.e. the animal's respiratory disease state).

For example, in some embodiments, the processor may be programmed to operate a mode of operation for analysing at least one infrared thermography images and to generate the TPV based upon at least five factors and patterns (four thermal factors and one thermal factor corrected for environment) about the images, such factors and patterns used to calculate or generate the comprehensive TPV about the animal, as described herein. As would be understood, the presently described TPVs are markedly distinct and more comprehensive from single thermal pixel temperature points conventionally used, such as with hand-held thermal radiometers, and from conventional thermal information obtained from infrared thermography images (e.g. as defined in U.S. Pat. Nos. 9,961,883, 9,955,672, and 9,565,837).

In some embodiments, without limitation, the presently described comprehensive TPV may be generated using the following formula:

$$TPV = T\text{Max} + SD(T\text{Max}) + \text{Mean }°\text{C.} + \Delta T(°\text{C.}) + \text{Residual}$$

wherein, TMax means a maximum temperature detected in the plurality of infrared thermography images, the area being determined to be the hottest area (i.e., the hottest temperature recorded from the image). In some embodiments, the TMax may be obtained from or about the animal's eye, said value then comprising the TMax of the eye. Although the TMax of the eye is demonstrated herein, it should be appreciated that the TMax may be detected about different anatomical areas, wherein, SD (TMax) means a calculation to indicate the extent of deviation for the TMax. For example, as may be understood, as an animal enters into a disease state, it's temperature will change (i.e. increase). Herein, the SD calculation may be indicative of changes in the TMax, i.e. in the dispersion of temperature about the animal;

wherein, Mean ° C. means an overall mean temperature taken about the animal, for example of the animal's skin (e.g. cheek area). Herein, the mean ° C. may comprise obtaining an overall temperature from the at least one infrared thermography images, the overall temperature obtained from an area approximately 3 cms ventral and approximately 3 cms distal to the eye. An overall average temperature (Tavg) may be measured in order to detect, for example, an overall symmetry profile about the animal (e.g. as the animal enters a disease state and becomes, the overall asymmetry normally observed in an animal's face/body may dissipate, the mean temperature becoming more symmetrical);

wherein, ΔT means the difference between the TMax (e.g. for the eye) and the Mean ° C. (e.g. of the skin), said difference decreasing, for example, where the animal enters a disease state and becomes hotter due to fever; and wherein, Residual means the expected mean temperature values, such expected values determined by, for example, a linear regression analysis. In some embodiments, the linear regression analysis may comprise comparing the environmental temperature (TEnv; y axis) against the temperature obtained from cohort group of normal animals (TAni; x axis). Residual may also be referred to as an "adjusted temperature" such that, for example, the overall TPV is adjusted/corrected for any changes in the animal's temperature due to its environmental conditions (e.g. where the animal may be outside a thermal neutral zone). The Residual value may be determined using normalized temperature values taken over time and at different environmental conditions, such that a reference value may be obtained and then used to predict Mean ° C.

More specifically, FIG. 1 provides an example image of a thermal profile value (TPV) about an animal, where the animal is determined to be in a true-negative (TN; FIG. 1A) biological state, and then where the same animal is determined to be a true-positive (TP; FIG. 1B) biological state. The images are provided for the same animal as it was followed through a healthy state to a state of viral infection. In the TN state, the animal's average temperature was at 34° C. (SD 11.8 Delta T 22.8) and in the TP state, the average temperature was 36.1° C. (SD 5.2 Delta T 17). Measurements taken were ear aspect 90 degrees to median Frontal Plain (FIG. 1A) and ear aspect 60 degrees to Frontal Plain (FIG. 1B). The images shown demonstrate difference in the thermal value for the eye vs the skin or the delta T as the disease progresses.

Figure 2:
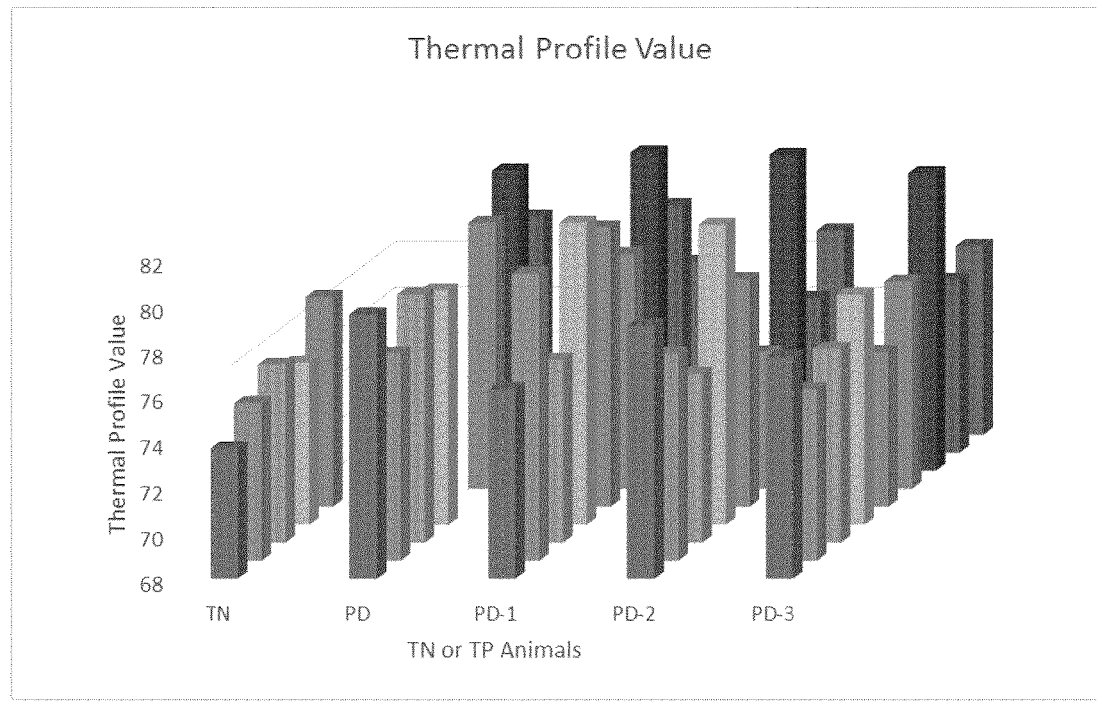
FIG. 2 shows thermal profile values for True Positive (TP) and True Negative (TN) animals for biologically important states, such as respiratory disease, according to embodiments.

As above, having regard to FIG. 2, TPVs generated according to embodiments had an r value or correlation coefficient with the TP or TN health status of r=0.93 (r squared of 0.86) at P<0.01. More specifically, the presently described thermal profile values were generated using the following formula:

$$\text{Thermal Profile Value} = \text{Eye Max value}(°\text{C.}) + \text{Eye SD} + \text{Skin value}(°\text{C.}) + (\text{Eye} - \text{Skin})(°\text{C.}) + \text{Residual},$$ where Residual=difference between expected eye max temperature (° C.)(based on Environmental Temperature)vs observed or actual eye max temperature(° C.).

Having regard to FIG. 3, 'PD' refers to pull-day or the day the animals were observed to be symptomatic clinically (described in more detail below). Advantageously, the presently generated TPVs were found to be indicative of an animal's disease state a minimum of three days earlier (pull day 3, PD-3) than conventional methods (spot detection of the eye or cheek), where r values were between 0.7 and 0.9, depending on the day. That is, the presently obtained TPV maintained an r value of 0.84, denoting a disease state in animals at least three days before clinical signs were observed, such r value being significantly greater than the detection by measuring eye or skin temperature alone with r values of 0.051 and 0.014, respectively.

In addition to the foregoing TPV generation, conventional methods of diagnosing a disease state in animals were used as control data. For example, laboratory testing of each animal included serology, hematology, cortisol and core body temperature (serology values conducted by Prairie Diagnostic labs, Saskatoon, SK, Canada). BVD and IBR were conducted via serum neutralization procedures and Corona, PI3 and BRSV by ELISA. Hematology was conducted on whole blood using a Celldyne model 3700 analyser (Abbot Labs, Mississauga Ontario). Cortisol was assessed by ELISA, and whole blood used for hematology assessment was collected by venus puncture using restrained calves and procedures as required by the Canadian Council of Animal Care Codes of Practice for the Care of Beef Cattle.

Animals were also monitored for clinical scores, as would be known in the art. The animals were classed as TP or TN based on a defined "gold standard" scoring system developed in concert with veterinary pathologists. The analysis included five-point scores for respiratory function, digestive function, disposition and temperature. Clinical scores were designed to identify bovine respiratory disease (BRD) and were based on the appearance of four criteria as follows:

Respiratory Insult: (0-5): 0=no insult, normal breath sounds (NBS); 1=Very Fine Crackle (rale) (VFCR) on auscultation and/or a moderate cough; 2=Fine Crackle (subcrepitant) (FCR) on auscultation and/or a moderate nasal discharge and moderate cough; 3=Medium Crackle (crepitant) (MCR) on auscultation and/or a moderate to severe viscous nasal discharge with cough; 4=Course Crackles (CCR), tachypnea (>15% of the norm) and/or a severe discharge with respiratory distress and obtunded lung sounds; 5=CCR with dyspnea, tachypnea, marked respiratory distress and/or lung consolidation.

Digestive Insult: (0-5): 0=no insult, normal, eating and drinking; 1=mild or slight diarrhoea with slight dehydration (<5%) and reduced eating; 2=moderate diarrhoea with 10% dehydration and reduced feed intake (<50%); 3=moderate to severe diarrhoea with 10% or less 6 of feed intake and more than 10% dehydration; 4=severe diarrhoea, and less than 10% of normal feed intake. 5=severe diarrhoea and not eating, not drinking and dehydrated.

Temperature Score: Core Temperature (rectal) (0-5): 0=<37.7; 1=37.7-38.2; 2=38.3-38.8° C.; 3=38.9-39.4° C.; 4=39.5-40.0° C.; 5=>40° C. Rectal or core temperatures for the calves were collected at the start and end of the study only as this required the capture and restraint of the animals.

Disposition or Lethargy Score: (0-5): 0=no lethargy, normal posture; 1=mild anorexia or listlessness, depressed appearance; 2=moderate lethargy and depression, slow to rise, anorectic; 3=recumbent or abnormal posture, largely depressed; 4=prostrate, recumbent or abnormal posture; 5=death.

In addition, serology and cortisol values were monitored as well as acute phase proteins on a subset of animals. For TP an animal had to display three or more of: a core temperature of >40 C, a white blood cell count of <7 or >11×1000/µl (leucopenia or leukophilia), a clinical score of 3 or higher and a neutrophile/lymphocyte ratio of <0.1 or >0.8. A TN was defined as an animal displaying 1 or fewer of the above. While there is debate regarding what constitutes a "gold standard" there is nonetheless general agreement that the method used displayed high utility for identifying TP and TN animals.

The day animals were identified by a veterinarian as symptomatic, ill and treated is referred to as a "pull day" (PD), and consists of the day that the presently described analysis was performed. There were five animals with TN characteristics and nine with TP characteristics, as confirmed by the foregoing conventional tests, such animals found to have a high degree of confidence regarding health status and that displayed elevated serology titter for at least one virus. As above and as shown in FIG. 3, the presently generated thermal profile value had higher r values when compared to single thermal measurements taken from the eye or skin. Accordingly, the foregoing demonstrates that the presently generated TPVs provide a more comprehensive and accurate representation of an animal's health status. Again, advantageously, the presently described TPVs can be generated automatically and are compatible with internet-based cloud data systems.

In addition, the facial aspect or kinematic expression of the animal can also be detected, i.e. where a postural change may be displayed by the angle of the ears with a flatter, more depressed position of the ear in the infected animal. For example, the kinematic expression of a TN animal may appear normal (ear position is normal; FIG. 1A), whereas the kinematic expression of a TP animal appears abnormal (ears are depressed or flatter; FIG. 1B). For the first time, the generation of a comprehensive TPV from the combination of thermal pattern information and behavioural aspects are shown to improve the predictability and detection of biologically important states in an animal. The combined thermal pattern and behavioural profile approach is statistically and diagnostically superior to conventional practice in the health care systems for animals and humans, such practices primarily using a single pixel or low-resolution scan device or simply clinical scores.

According to embodiments, the foregoing example demonstrates that the present apparatus and methodologies may be pertinent in connection with the early and effective detection of disease states in an animal (e.g. viral induced disease states, such as coronavirus induced COVID-19). By way of example, with the so-called R naught (R0) value for COVID-19 reported at between 1.5 to 3.5, each day of advanced screening and quarantine of infected individuals can potentially save the exposure of many other individuals. It is contemplated that the present described thermal profile approach has the capability for disease detection and warning, even where individuals may be asymptomatic or not-yet-symptomatic.

Herein, it is contemplated that an automated, non-invasive and internet driven infrared thermography scan station could be developed utilizing commercially available cameras (e.g. Biondi camera) which could incorporate thermal profile approaches developed with other mammalian models. As above, facial kinematic characteristics could be simultaneously collected. Thus, the present apparatus and methodologies could well serve as a rapid screening technology based on parallel testing, augmenting a subsequent, serial testing with appropriate Elisa or similar test for specific pathogen presence. For example, it has been shown that parallel testing, wherein two or more methods are used at the same time, will increase the sensitivity of TP detection and serial testing (one method and then another methods afterwards) will increase the specificity of TP detection. Such screening may not only be more accurate but may also enable significant saving of time and resources (e.g. test kits and lab technician time); provided that appropriate test numbers would need to be undertaken to meet proper statistical power function requirements (number of people). It would be noted that it is far easier to scan people than most animals, and the present screening could assist in directing scarce resources for further testing.

Example 2: This Example demonstrates the use of the present apparatus and methodologies for the detection, diagnosis, and/or treatment of biological states in animals, wherein the apparatus and methodologies comprise improved means for screening for the animal's metabolic efficiency. As will be described, a comprehensive thermal pattern about the animal is generated, said thermal patter indicative of the animal's health and metabolic efficiency.

As above, the production of high-density protein of animal origin is important for the maintenance of human health, as reflected in the growing demand for same globally. Such information is conventionally determined using indirect techniques like calorimetry or measuring food intake at feed stations, however, these techniques are quickly becoming outdated and are expensive. Moreover, these techniques are retrospective in that the animal must be monitored for a significant time before any efficiency ranking can be accomplished.

Apparatus and methodologies for earlier and more effective detection of an animal's metabolic efficiency are needed to select animals having higher efficiency, and a lower cost of production, and also to lower Green House Gas (GHG) production often referred to as the carbon footprint. Understanding how to measure these properties is important as a method for the genetic selection of more efficient animals and hence to reduce the anthropogenic GHG impact of producing high density protein. According to embodiments, apparatus and methodologies for identifying important biological states in an animal are provided, the biological state comprising steady and/or non-steady biological states (e.g. metabolic efficiencies of animals). In addition to the presently described apparatus and methodologies, by way of control data, conventional methods of determining metabolic efficiency including feed intake and weight gain were also monitored.

First, as above, TPVs of the animals can be generated in order to determine the animal's overall health. Herein, TPV may comprise=Eye Max value (° C.)+Eye SD+Skin value (° C.)+(Eye−Skin) (° C.)+Residual, where Residual=difference between expected eye max temperature (° C.) (based on Environmental Temperature) vs observed or actual eye max temperature (° C.). Advantageously, when TPV is used as a bio-surveillance tool, it is found that approximately 2% of animals are found to be of abnormal health. Where the animals are found to be unhealthy, or not healthy, they can then be assessed for their metabolic efficiency.

In this Example, animals (swine) were raised in a genetics herd by Hendrix Inc. from approximately 30 kg to 130 kg in a typical swine facility representative of the industry (at a nucleus site, Kenlis, Saskatchewan, Canada). A feed station (NeDap®) was used to monitor the animal performance wherein the feed consumption and weight gain were routinely measured according to specified operating procedures for these feed stations. This period of time was approximately 9 weeks.

At least one automated broad-spectrum infrared thermography (IRT) imaging device (e.g. a FLIR A65 high resolution camera) was positioned at or near the animal's feed station (e.g. mounted approximately 1 meter above an enclosure, such as a restraint cage). Each at least one imaging devices captured a plurality of images daily, several times per day, from the dorsal region of each animal as they attended the station, the device being triggered automatically by the animals entering the station. In some embodiments, the plurality of images were collected at a rate of approximately 20 images per second and the assessment of each animal required approximately 20 seconds. Each of the plurality of images were received by the at least one imaging device at a central processor, the processor programmed to provide a mode of operation for analysing the plurality of infrared thermography images for basic temperature values (Maximum, Mean and Minimum Temperature) using commercially available software (example FLIR Research IR) and to generate a comprehensive thermal pattern or map about the animal therefrom.

Having regard to FIG. 4, example thermal coat patterns or maps from at least two animals are shown, wherein one animal is metabolically inefficient (left) and one animal is metabolic efficient (right). The at least one infrared thermography images were analysed and were determined to contain a completely different thermal coat patterns for metabolically efficient animals (right) as compared to metabolically inefficient animals (left). In some embodiments, the processor may be operative to provide a mode of operation for analysing a the images about the animal and to select portion of the animal's dorsal region from the image, said region being used to provide a mean temperature (TMean) about the animal, which then can be processed to correct for the animal's metabolic size as a means for ranking the animal's metabolic efficiency (e.g. as would appreciated, an animal's metabolic rate scales to the % power of the animal's mass). The resulting mode of operation thus providing a comprehensive thermal coat pattern about the animal, said pattern being indicative of the animal's metabolic efficiency.

As will be described below, the foregoing thermal coat patterns to detect metabolic efficiency in animals were confirmed using conventional methods, such as Feed Conversion Efficiency (FCE), wherein the metabolically efficient animal had an FCE of 1.7 kg feed required per kg of weight gain (right), and the metabolically inefficient animal had an FCE of 3.2 kg feed required per kg of weight gain, wherein such conventional methods being further accounted for in order to generate an overall thermal efficiency index, 'TEI' (such that animals can be ranked by their mean temperature and corrected for their TEI). By way of explanation, the metabolically efficient animal shown on the right may, during a typical 100-day performance period, require some \$35-\$50 USD less feed and produce some 700 kg less $CO_2$. Accordingly, the present methods provide animal caregiver's an accurate and efficient means for determining an animal's metabolic efficiency, allowing for the ranking of animals according to their efficiency and the possible culling of those less efficient from the herd.

Having regard to FIG. 5, the processor was further operative to provide a mode of operation for further analysis of the thermal coat patterns or maps about the animal to generate a comprehensive thermal histogram, the thermal histograms providing few thermal histogram bins in higher temperature areas where the animal is more metabolically efficient (right) as compared to the animal that is metabolically inefficient (left). The presently demonstrated thermal coat patterns can also be generated by determining asymmetries or differences in the degree of thermal symmetry (i.e. skews) in the pixel distribution. As such, the presently analysed infrared thermography images provide a different thermal topography in animals with differing metabolic efficiency performance. Advantageously, the foregoing detection of metabolic efficiency may be determined in a matter of seconds or minutes, and may further be provided without first having to induce the animal into a non-stead state (e.g. without having to take the animal off-feed). Moreover, it is contemplated that the foregoing detection of metabolic efficiency and/or TEI may be heritable.

Historically, the difference in thermal parameters between animals with different efficiencies has been defined by conventional parametric statistics such as measures of central tendency including means and medians with differences among individuals tested with least squares means statistics. However, as demonstrated in FIG. 4, the present apparatus and methodologies provide different thermal topographies between animals having different metabolic efficiency performance. Herein, it should be understood that the present apparatus and methodologies can be used to define thermal patterns including, but not limited to, different thermal histograms as shown in FIG. 5. The more efficient animal demonstrates fewer thermal histogram bins in the higher temperature area. The thermal coat pattern can also be defined by observing how asymmetrical or skewed or the difference in degree of thermal symmetry in the pixel distribution.

As above, in addition to the foregoing thermal coat pattern profile, conventional methods of determining metabolic performance were used as control data, such tests meeting current industry performance monitoring standards wherein an animal's feed intake and weight gain is monitored over about an 8 to 12-week period. For example, known tests comprise assessing the animal's performance using the following factors:

Feed Conversion Efficiency (FCE) defined as the amount of feed (kg) required to enable a gain in weight (Kg feed/Kg weight gain).

Residual Feed Intake (RFI) defined as the amount of feed required by an individual animal to gain one kg of weight compared to the amount of feed expected to be required (Actual Feed Consumed/Expected Feed Consumed).

Average Daily Gain (ADG) defined as the average amount of weight gain per day by an animal over a test period.

Feed Intake (FI) defined as the average amount of feed consumed by an animal per day over a test period. This quantitative amount can be expressed as a dry weight or as is.

Residual Intake and Gain (RIG) defined as the optimal animal weight gain per amount of feed intake. This value identified the animals that are gaining the most weight for the least amount of feed or are the most efficient at the highest gain.

Having regard to FIG. 6, the utility of the present generated thermal patterns in identifying animals having different metabolic efficiencies can be determined using a basic correlation test between a measure of metabolic efficiency, RIG, and one measure of thermal symmetry (referred to as TSym, where TSym is a measure or coefficient of skewness across the dorsal view of the animal). The statistical correlation value can be calculated using commercially available software (e.g. Medcalc® Statistical Software version 19.5.3, MedCalc Software Ltd., Ostend, Belgium). The results show that the thermal distribution of pixels is not normal, but is asymmetrical, with a statistically significant relationship between the two measurements (r=−0.4, P<0.0001).

Having regard to FIG. 7, to further illustrate the utility in the presently generated thermal profiles or patterns, a regression equation was used to measure the contribution or statistical weight of different thermal parameters with a measure of metabolic efficiency such as RIG, such that the additive impact of the thermal symmetry value can be seen. As shown, the partial weight added to the regression equation from the thermal symmetry value in this population of 334 animals (Duroc Sires) is approximately 15%.

$$RIG=2.96+[(-10.45)(TEI)]+0.24 \text{Mean}T+[(-0.66)(TSym)] \quad \text{Regression Equation}$$

For the first time, the generation of a thermal pattern or profile and thermal symmetry is shown to improve the determination of metabolic efficiency in animals. Advantageously, the presently described thermal patterns or profiles are non-invasively generated in approximately 20 seconds, rather than the 9-14 weeks required for conventional techniques. The presently generated pattern provides a partial correlation with a measure of efficiency and growth (RIG) of some 15% to 30%, i.e. the strength of a regression equation being increased by adding this factor. The importance of utilizing this value is that animals with greater metabolic efficiency will have a lower GHG footprint.

According to embodiments, the foregoing example demonstration that the present apparatus and methodologies may be used to develop an automated, non-invasive and internet compatible infrared thermography scan station utilizing commercially available cameras (e.g. FLIR, Biondi Engineering Inc.) which could incorporate thermal profile approaches developed with other mammalian models. As above, thermal 3D kinematic characteristics such as ear profile and angle differences, can also be simultaneously collected and analysed. Thus, the present apparatus and methodologies could well serve as a rapid screening or ranking technology for important biological states in animals.

Example 3: This example demonstrates the use of the present apparatus and methodologies for the detection, diagnosis, and treatment of biological states in animals, wherein the biological state comprises at least one steady or non-steady state, such as pregnancy. As will be described, a comprehensive thermal pattern about the animal is generated, said thermal pattern indicative of at least one biologically important state in an animal.

As above, attempts to optimize the early detection of reproductive states in animals have utilized, without limitation, activity monitors (e.g. pedometers), rectal temperature using mercury thermometers, and intra-vaginal temperature loggers in tie-stalls. Unfortunately, such attempts have yielded contradictory results with varying coefficient of variation in core body temperature Apparatus and methodologies for earlier and more effective detection, diagnosis of pregnancy in animals are needed.

According to embodiments, apparatus and methods for identifying important biological states in an animal are provided, the biological state comprising pregnancy. In addition to the presently described apparatus and methodologies, by way of control data, conventional trans-rectal ultrasonography was also used in order to confirm pregnancy and cyclicity in animals.

In this Example, the results of two experiments are provided, the first experiment showing existing data from radiated temperature and behaviour biometric comparisons between pregnant cows (Pregnant) and cyclic cows (Cyclic), and the second experiment showing results from forty Holstein cows.

Figure 8A:
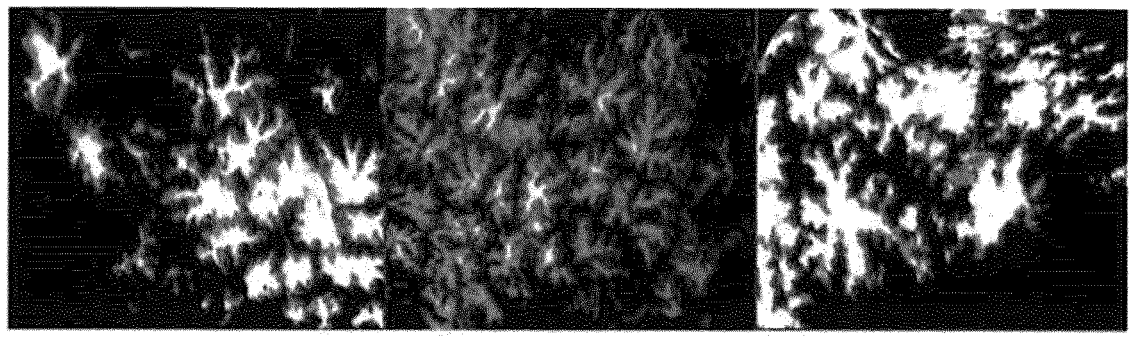
FIG. 8A), or the TCPs not detected when an animal is not in a biologically important state (i.e. not pregnant.
Figure 8B:
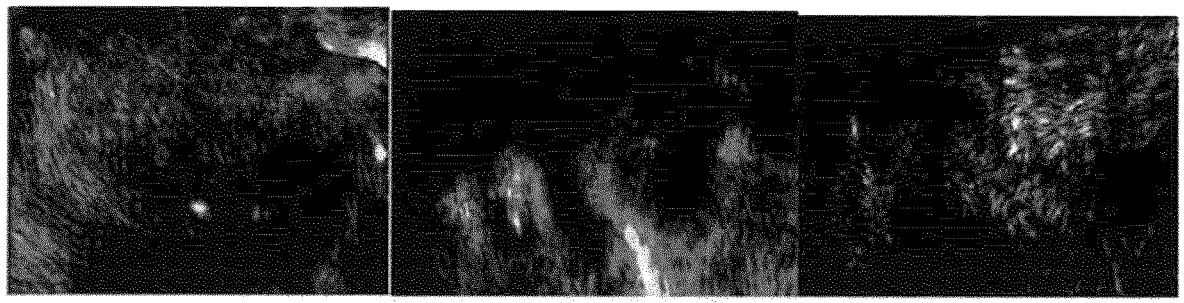
FIG. 8B)

In the first experiment, having regard to FIGS. 8A and 8B, at least one broad-spectrum infrared thermography (IRT) imaging device was used to obtain a plurality of images about an animal. The plurality of images were received at a central processor for processing and, as shown in FIGS. 8A and 8B, the presence of specific thermal coat patterns (TCPs) were detected and used to generate at least one comprehensive thermal profile about the animal, said profile being an indicator of pregnancy in the animal (e.g. the detection of multi-branched stellar dendrite or 'tree-like' shaped patterns to indicate pregnancy). In some embodiments, central processor received the plurality of images about the animal, and analyzed same to detect the TCPs in a binary fashion as either present (score 1, where the animal is pregnant; FIG. 8A) or not present (score 0, where the animal is not pregnant; FIG. 8B) for all animals over 9 days (n=36; Pregnant=18 and Cyclic=18).

An ideal estrus detection requires a flagging system in order to identify animals in estrus, which in most cases requires a reference value (e.g. a threshold or cutoff value) based in a biometrical parameter(s). The ideal estrus detection test should discriminate unerringly between estrus (True Positives—TP) and non-estrus (True Negative—TN) and should be capable of flagging animals on a regular basis, such as daily. In addition, ideal estrus detection methods should comprise some sort of scoring index to evaluate the accuracy of the estrus alert. The most common diagnostic analysis for evaluating accuracy is a receiver-operating curve (ROC), which uses a balanced proportion of sensitivity (Se) and specificity (Sp).

Figures 9A, 9B:
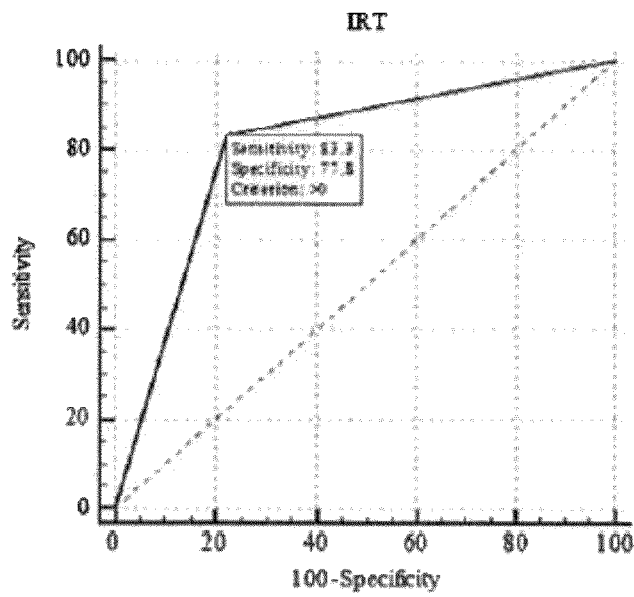
FIG. 9 shows the results of a receiver operant characteristics analysis (i.e. ROC curve analysis) demonstrating sensitivity and specificity of the detection of the TCPs shown in FIG. 8.

Accordingly, the accuracy of the foregoing detection methods of detecting TCPs as an indicator of pregnancy was determined using an evaluation of sensitivity (Se) and specificity (Sp) using an ROC analysis (FIGS. 9A and 9B). By looking at the TCP between equal numbers of pregnant and cyclic cows, 80.56% (n=29 cows) of the cows were correctly identified as pregnant and 19.444% (n=7 cows) were incorrectly identified as pregnant (e.g. False Positive—FP).

Accordingly, results from the first experiment demonstrate that the presently described apparatus and methodologies of use for identifying at least one biological state may be an ideal method for rapidly and accurately detecting estrus and/or pregnancy in animals.

In the second experiment, an analysis of forty lactating Holstein cows was performed, the animals having parities ranging from 1 to 5 and gestation stage ranging from 60 to 210 days. All animals were divided in 5 groups of 8 cows each (n=40 total) as per gestation stage in a cross-section study design, as follows:

Group 1 cycling cows (Cyclic) were not pregnant and days in milk (DIM) ranged from 30 to 60 days; Group 2 consisted of pregnant cows 60 to 90 days in gestation (DG); Group 3 included pregnant cows 12 0-156 DG; Group 4 consisted of pregnant cows 180 to 210 DG. The $5^{th}$ group of animals were between 262 and 285 days of pregnancy and thus were obviously pregnant (and no infrared images about these animals were taken). Cows were selected in random order and the experimenter was blind to the gestation stage, DIM and parity of each cow to avoid any potential bias. University of Alberta DRTC DairyComp 305 records (CanWest DHI, Alberta, Canada) were used to select an equal number of cows within each of the groups described. Calving, DG, dairy milk production and DIM were recorded on a daily basis and pregnancy diagnosis was performed by local veterinary services at 30 and 60 DIM.

Again, at least one automated broad-spectrum infrared thermography (IRT) imaging device was positioned at or near the animal. In this experiment, the plurality of thermal images were recorded from two anatomical locations, namely, the animal's rump and flank. In some embodiments, the appropriate distance and appropriate angle of the plurality of images was ensured so as to obtain high quality thermal images, such distances and angles being confirmed using a laser tool (e.g. GLM15 50 ft laser series, Robert Bosch Tool CO. IL, USA). In some embodiments, the thermal images were captured from an approximate distance and angle of 1 m perpendicular angle from the animal's rump and flank. In some embodiments, the plurality of thermal images were recorded for one day per animal at different time periods, e.g., at morning (0700), midday (1100), and afternoon (1500), using a thermal imaging device as described herein.

In some embodiments, prior to each thermal image being captured, ambient temperature and the percent relative humidity were recorded at each animal's stall using an anemometer, hygrometer, lux meter, and thermometer (e.g. a 72-7595 4-in-1 device; TENMA™ distributed by Newark Chicago, IL). In accordance with recommended procedures for scanning live tissues, in order to calibrate each at least one thermal imaging device, the emissivity was set to 0.98. To confirm pregnancy and cyclicity of cows, each cow's reproductive tract was scanned prior to the study period using trans-rectal ultrasonography (Ultrasound ALOKA SSD-500 3.5 MHz linear transducer ALOKA Col., LTD., Tokyo, Japan) in order to confirm pregnancy in cows that had been previously diagnosed pregnant and to confirm cyclic-non pregnant cows.

Again, the plurality of thermal images obtained by the at least one thermal imaging device were received at a central processor for processing (e.g. said processor being programmed to operate FLIR ResearchIR; FLIR Systems Ltd., Burlington, Ont, CA). In some embodiments, the processor may be programmed to provide a mode of operation for determining and analysing a maximum radiated temperature (max/temp) recorded from each flank and rump location, such max radiated temperature of each location being recorded from pixel determined to be the hottest pixel in order to eliminate confounding thermal data from the convection of debris with different emissivity to the environment.

Figure 10:
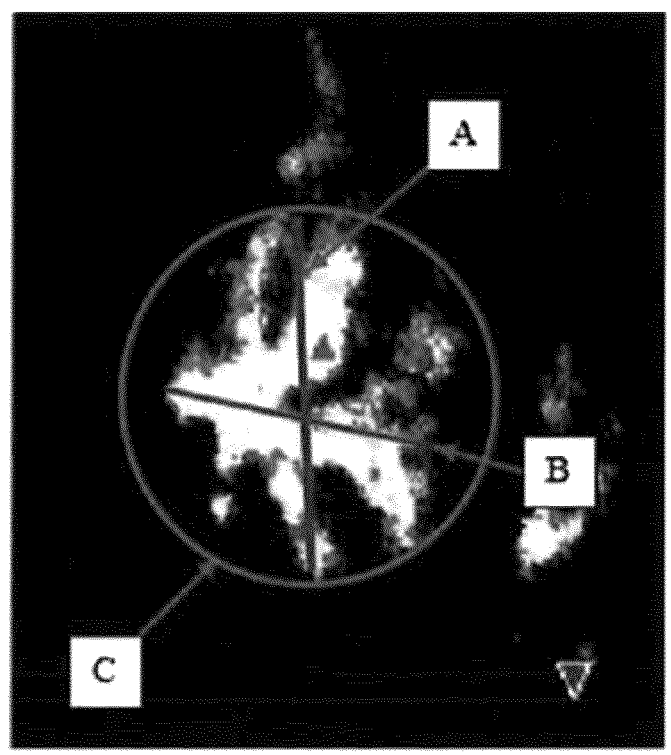
FIG. 10 depicts an example TCP as detected from a plurality of infrared thermography images about an animal, the TCP being indicative of at least one biologically important state in the animal.

For example, having regard to FIG. 10, the thermal image analysis was conducted by measuring the number of pixels inside detected thermal coat pattern areas (TCP area). A region of interest (ROI) for each detected TCP was generated and then analyzed using the TCP area (i.e. the total amount of pixels inside an ellipse covering the entire ROI (circled area 'C'; FIG. 10). In some embodiments, the length of the ROI of the TCP ('A'; where length is the amount of pixels of the vertical diameter from the detected TCP) and width of the ROI of the TCP ('B'; where width is the amount of pixels of the horizontal diameter from the detected TCP) were selected, and generated using a predetermined ROI as compared with gestation state, block, sample time, and parity.

In some embodiments, the TCP areas were then ranked for each animal, and the largest TCP in the thermal image was selected for each animal's scan period and used in the analysis of each IRT image. For example, having regard to FIG. 11, block effect had a significant level in most of the infrared thermography and pixel parameters, which may be attributed as a result of different ambient temperatures, relative humidity and the allocation of the animals for their state of lactation where (A) provides recent calving and sick animals, (B) are 0-50 days in milk, (C) are 50-120 days in milk, and (D) 120—until the end of lactation. Parity had a significant effect on length and width of the TCP area however, not all the gestation groups showed an even parity groups. Sample time effect may be attributed to the circadian rhythm and ambient temperature.

Figure 12C:
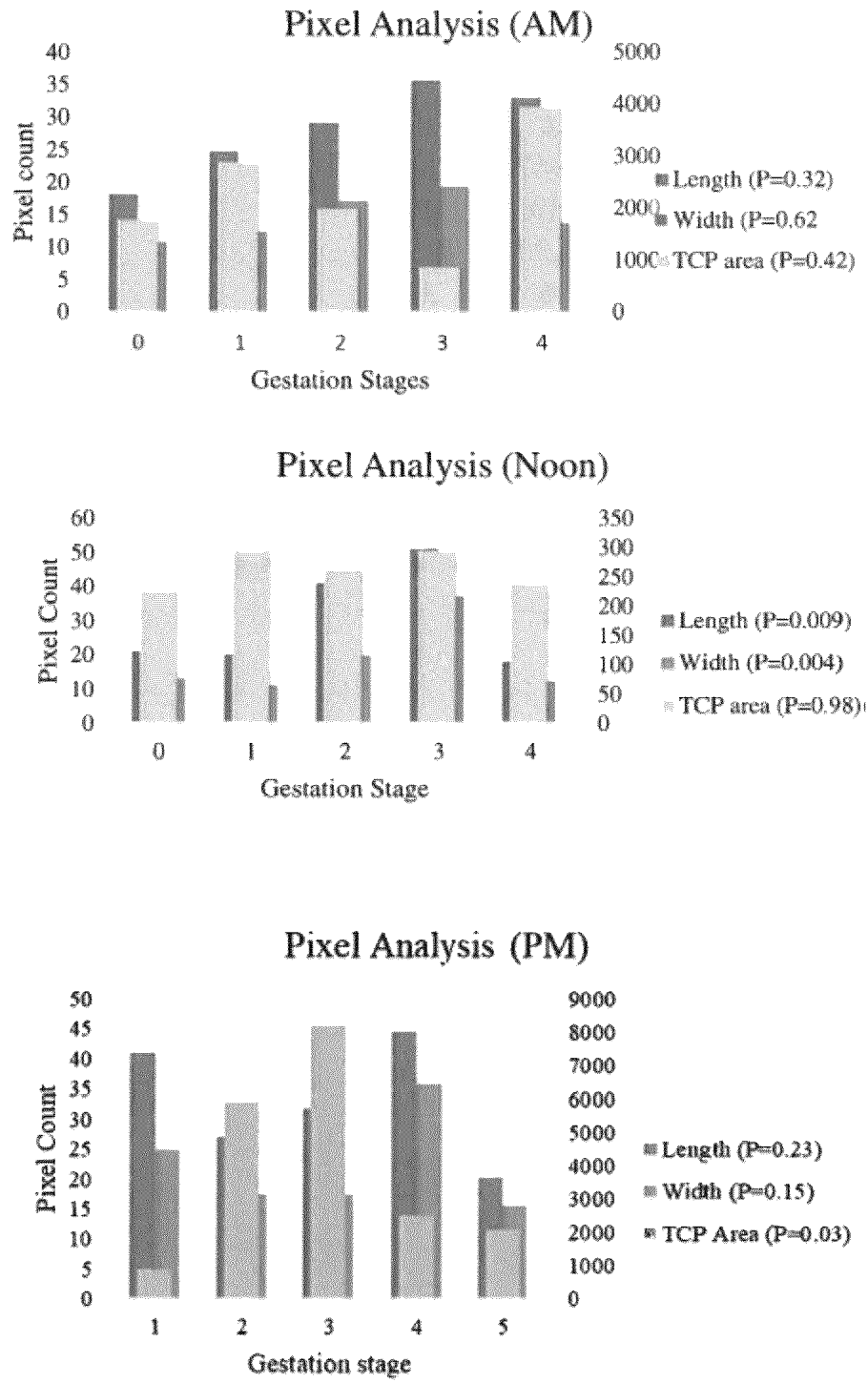
FIG. 12 provides the results of the Shape and Diffusion scale analysis, where FIG. 12A provides the randomized allocation of gestation groups among animals (frequency is denoted in the first row followed by percentage in the next row), and FIG. 12B provides the diffusion scale and the randomized allocation of gestation groups, and their association between diffusion and gestation (frequency is denoted in the first row followed by percentage in the next row), with additional results shown in FIGS. 12C and 12D, according to embodiments.

In addition, having regard to FIGS. 12A and 12Ba photographic scale analysis was performed using shape and diffusion categories (Scales 1 and 2) for each of the plurality of IRT images from different sample days in duplicate (a second examiner categorized the IRT image with >90% of agreement between examiners). The photographic scale analysis was conducted by calculating the frequency (Proc Freq in SAS 9.4) of Shape and Diffusion for each gestation stage. Having regard to FIG. 12A, the closest association was observed between Shape 1 and Gestation group 4, and Shape 2 with Gestation group 2. Having regard to FIG. 12B, associations between Diffusion and Gestation groups were observed between Diffusion A with Gestation group 4, Diffusion B and Gestation group 1 and Diffusion C and Gestation group 0.

Figure 13A:
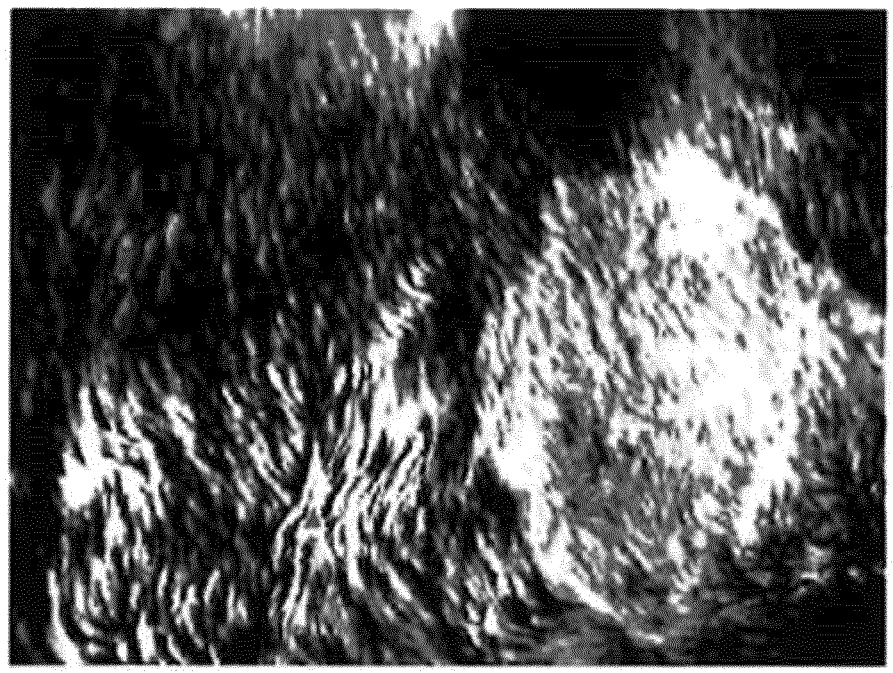
FIG. 13 provides example images of the presently obtained infrared thermography images, such images being analyzed to determine shape category for TCPs of the animals, according to embodiments.
Figure 13B:
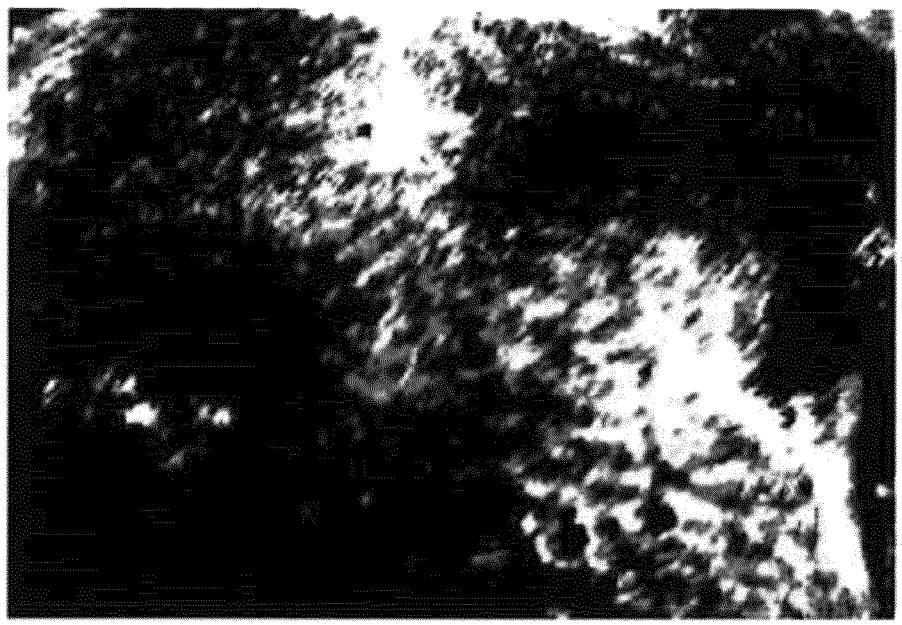
Figure 13C:
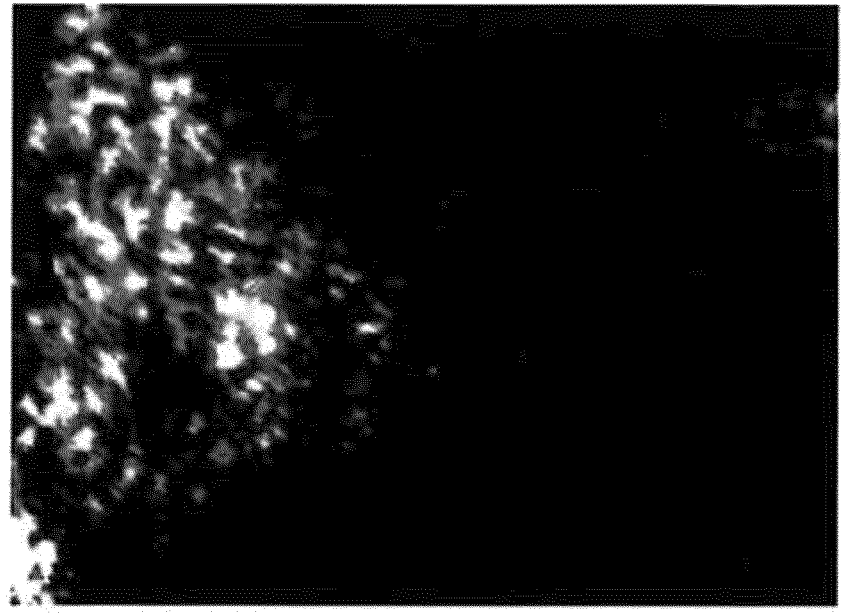
Figure 13D:
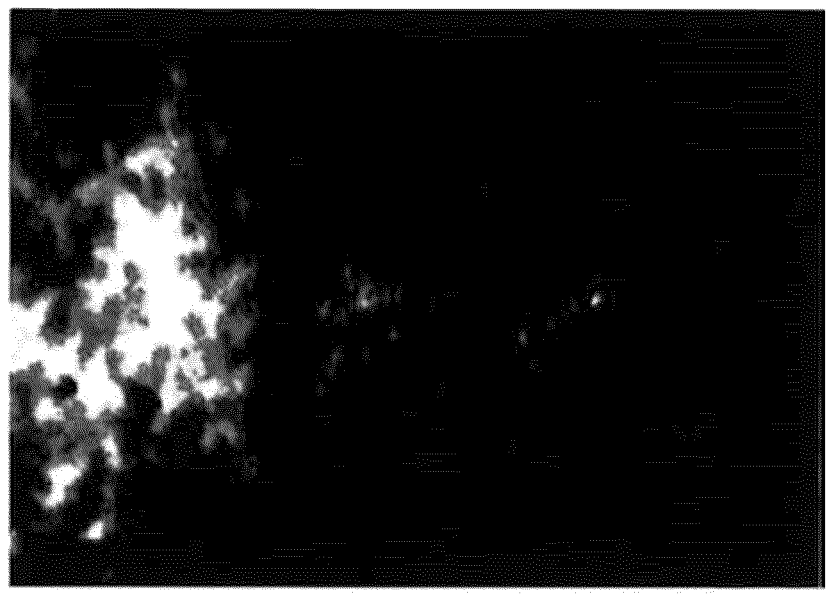
Figure 13E:
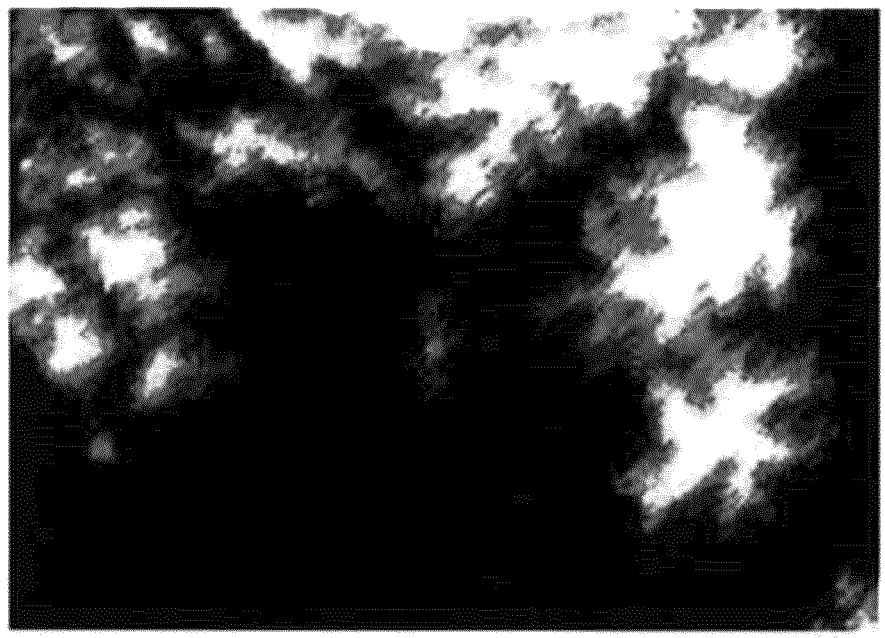
Figure 13F:
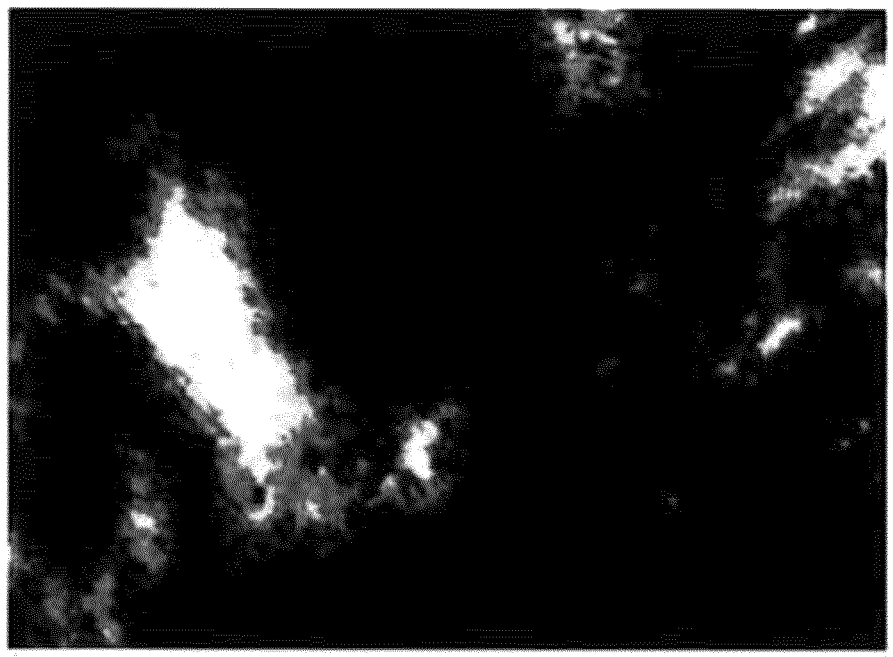

Having regard to FIGS. 13A-F, examples of the presently obtained infrared thermography images are provided, such images being processed to determine shape category for TCPs according to a predetermined scale, the scale being developed to automatically and reliably differentiate between types of thermal coat pattern shapes (e.g. the TCPs being shown from the animal's the rump area). For example, in some embodiments, the present scale may provide a score of Non-Legible (1) where the TCP contains no defined structure, and the hair/coat of the animal is easily observed (FIG. 13A); Irregular (2) where the TCP contains small structures that are not well defined, the division between the structures not always discernable (FIG. 13B); Irregular Defined Pick (3) where the TCP contains small defined structures separated by each other (FIG. 13C); Stellar Dendrites (4) where the TCP contains well defined stellar shape with brunch alike crisp structures (FIG. 13D); Simple Star (5) where the TCP contains star alike shape with no peripheral crisp structures (FIG. 13E); and Spotted Area (6) where the TCP contains large cluster shapes with no stellar structures (FIG. 13F).

Having regard to FIGS. 14A-C, examples of the presently obtained infrared thermography images are provided, such images being processed to determine spread of the TCP according to a predetermined scale, the scale being developed to automatically and reliably differentiate between types of thermal coat pattern spread. For example, in some embodiments, the present scale may provide a score of Non-Legible (A) where the TCP spread contains a non-obvious pattern present with the hair/coat of the animal easily observed (FIG. 14A); Diffused TCP (B), where the TCP spread contains small structures covering the entire thermogram area (FIG. 14B); and Closter (C) where the TCP spread contains large structures present in some areas of the thermogram (note: size of the structures can be variable however, do not cover the entire thermogram).

Although the foregoing analysis comprises one manner of detecting a thermal coat patter about an animal, the pattern being used to generate a thermal profile value, it is contemplated that any other appropriate means known in the art may be used.

According to embodiments, the foregoing example demonstrates that the present apparatus and methodologies provide an effective, rapid and reliable means for detecting biologically important states in an animal, such state comprising estrus and/or pregnancy. Herein, the presently described apparatus and methodologies of use may provide infrared-based detection, diagnosis, and treatment of at least one biological state in an animal, the apparatus and methodologies for use by a farmer or animal caregiver to obtain real-time health information about the animal. It is contemplated that any one of the biological states as described herein may be so identified, whether alone or in combination (e.g. estrus detection may be determined alone, or in combination with other biological states, such as disease detection). For example, the presently disclosed apparatus and methodologies may enable animal caregivers to obtain real-time health information about the animals without the need for a laboratory (e.g. progesterone assays) or veterinary services (e.g. ultrasound). The present embodiments provide sustainable, optimized and socially-acceptable means for monitoring animal health and wellbeing, such embodiments being highly adaptable and combinable with other uses for infrared thermography on site.

Example 4: This example demonstrates the use of the present apparatus and methodologies for the detection, diagnosis, and treatment of biological states in animals, wherein the biological state comprises at least one condition, such as estrus. As will be described, a comprehensive thermal pattern about the animal is generated, said thermal pattern indicative of at least one biologically important state in the animal.

In North America, the majority of dairy cows in commercial milk production are currently bred using artificial insemination. To enable this practice an estrus detection system must be used to identify when the animals are biologically at the right chronological point of their reproductive cycles (estrus). Current methods used for this purpose include the analysis of endocrine factors such as progesterone in the milk or the behavioural assessment of estrus behaviour determined by a bio-surveillance device or by human handlers. Unfortunately, current methods are prone to failure, resulting in the animals not becoming pregnant for at least another estrus cycle or longer. Such delays reduce milk output from the animals, costing hundreds of dollars per animal in lost milk revenue.

Reproductive technologies have partially addressed the challenges with early detection of estrus by using hormone-based treatment to induce estrus and/or to induce ovulation (e.g. fixed-time ovulation). However, as would be readily apparent, the use of hormone-based injections is invasive, increasingly lacks social acceptance, and is less cost effective (~$6/cow USD) than estrus detection methods (~$0.15/cow USD). Although detection of reproductive states based on radiated temperature from the vulva can achieve positive predictive value (as a measure of accuracy) when using motion and image analysis, none of the foregoing technologies have been successful in detecting estrus using a combination of thermal patterns and behavioural profiles about the animal.

Apparatus and methodologies for earlier and more effective detection, diagnosis of biologically important states in animals, such as reproductive cycles, are needed.

According to embodiments, apparatus and methods for identifying important biological states in an animal are provided, the biological state comprising a reproductive state (e.g. estrus).

In this Example, at least one automated broad-spectrum infrared thermography (IRT) imaging device (e.g. FLIR S60 high resolution camera (320×240 pixels)) was positioned at or near the animal's water station. Each at least one imaging devices captured a plurality of images daily, several times per day, as the animals attended the water station, the device being triggered automatically by the animals entering the water station.

Each of the plurality of images were received by the at least one imaging device at a central processed, the processor being programmed to provide a mode of operation for processing the images and generating a thermal profile value (TPV) about each animal therefrom, the TPV being indicative of the animal's biological state (i.e. the animal's reproductive state).

Figure 15A:
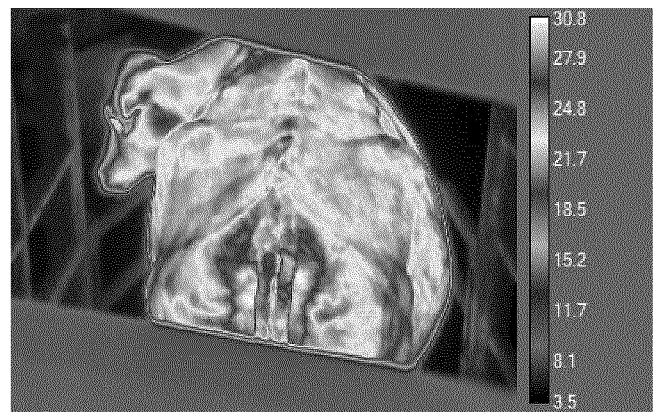
FIG. 15 provides infrared images about an animal according to embodiments herein.
Figure 15B:
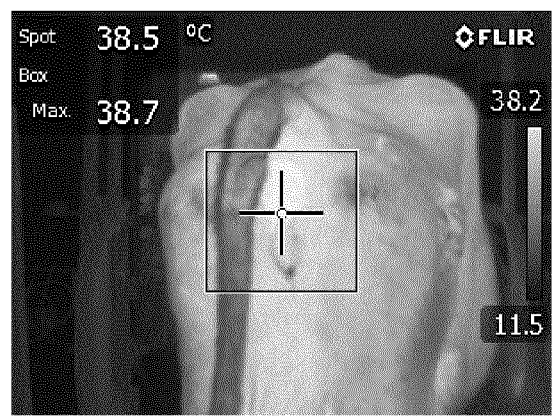
Figure 15C:
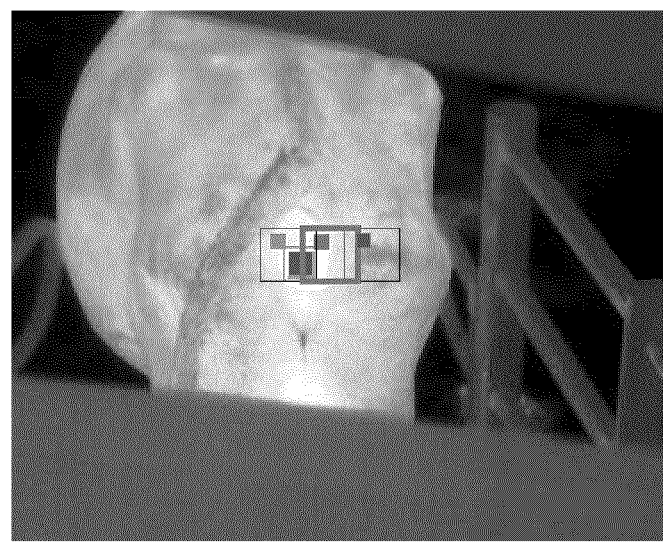

Having regard to FIGS. 15A-C, examples of the presently obtained plurality of infrared thermography images are provided. Each of the plurality of images may be processed to determine a TPV comprising a geometrical thermal coat pattern, i.e. a geometrical assessment of heat signals surrounding the animal's tail (distal view). In some embodiments, the assessment may comprise the automated analysis of one or more geometrically distinct areas in the image (e.g. rectangular areas about the image, where TMax for each distinct area, further denoted by red or green rectangular areas, may be determined and correlated with the biological state). For example, TMax in one distinct geometrical area (denoted as smaller rectangular areas; FIG. 15C) may be colder because the tail is positioned in that area, versus another distinct geometrical area where the vulva is detected as hotter (denoted as larger or bolded rectangular areas, FIG. 15C, as an indication of estrus).

Figure 16A:
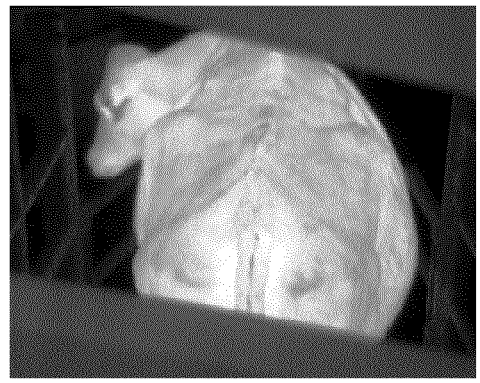
FIG. 16 provides images about an animal according to embodiments herein, the images showing no behaviour (FIG. 16A) and showing behaviour (FIG. 16B; tail movement).
Figure 16B:
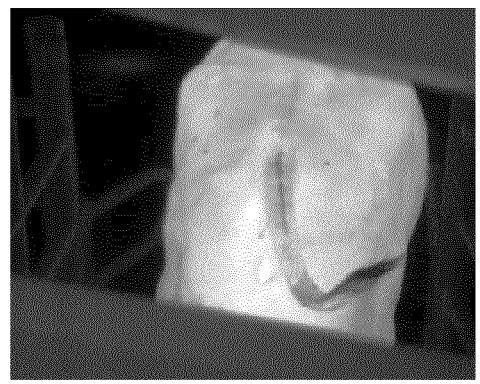

In some embodiments, when such thermal information is combined with at least one behavioural signal (e.g. tail position), a pattern can be seen more accurately, the pattern being indicative of a biologically important state in an animal. For example, the presently detected thermal patterns may be combined with behavioural information, where the behaviour is normal (e.g. tail position, FIG. 16A) or where the behaviour is observed (FIG. 16B, where the tail position has moved), in order to generate a more comprehensive thermal profile value about the animal.

According to embodiments, the foregoing example demonstrates that the present apparatus and methodologies provide an effective, rapid and reliable means for detecting biologically important states in an animal, such state comprising estrus and/or the onset of estrus. Herein, the presently described apparatus and methodologies of use may provide infrared-based detection, diagnosis, and treatment of at least one biological state in an animal, the apparatus and methods comprising the use of a plurality of infrared thermography images to simultaneously determine (from the same images) a thermal pattern about the animal as well as 3D-kinematics (i.e. changes in the frequency of postural angle due to pelvic tilting, pelvic shifts, foot strikes, and tail movements). In some embodiments, the present apparatus and methodologies may be operative to determine at least one biologically important state in an animal prior to the onset of the biological state, e.g. one or more days before ovulation.

Although a few embodiments have been shown and described, it will be appreciated by those skilled in the art that various changes and modifications can be made to these embodiments without changing or departing from their scope, intent or functionality. The terms and expressions used in the preceding specification have been used herein as terms of description and not of limitation, and there is no intention in the use of such terms and expressions of excluding equivalents of the features shown and the described portions thereof.

We claim:

1. A computer-implemented system for identifying at least one biological state in an animal, the system comprising:
   at least one high-resolution radiometric imaging device configured to obtain infrared thermography images about the animal, simultaneously capturing both
      thermal information, comprising at least one thermal coat pattern, and
      behavioural information, comprising at least one biomechanical feature,
   the imaging device being operably connected to a processor, and
   at least one processor configured to
      receive the infrared thermography images, and
      process the thermal and behavioural information from the infrared thermography images to calculate at least one thermal profile value, the thermal profile value being indicative of the at least one biological state in the animal.

2. The system of claim 1, wherein the thermal information comprises at least one of five factors.

3. The system of claim 2, wherein the at least five factors comprise four thermal factors about the animal and one thermal factor about the animal's environment.

4. The system of claim 1, wherein the processor is further configured to
   process the infrared thermography images to
      combine the behavioural information with the thermal information to generate the thermal profile value indicative of at least one biological state in the animal.

5. The system of claim 4, wherein the behavioural information may comprise a kinematic expression or anatomical aspect about the animal.

6. The system of claim 1, wherein the at least one infrared thermography images are collected automatically in real-time.

7. The system of claim 1, wherein the at least one biological state may be selected from the group consisting of a disease state, metabolic efficiency, and a reproductive state.

8. The system of claim 1, wherein the at least one imaging device is positioned at or near an enclosure.

9. A computer-implemented method for identifying important biological states in an animal, the method comprising:
   obtaining at least one infrared thermography images about the animal from a high-resolution radiometric imaging device, the at least one image simultaneously capturing both thermal information comprising at least one thermal coat pattern and behavioural information comprising at least one biomechanical feature about the animal,
   processing the thermal and behavioural information from the at least one infrared thermography image about the animal to
   calculate a thermal profile value, the thermal profile value being indicative of the at least one biological state in the animal.

10. The method of claim 9, wherein the thermal information comprises at least one of five factors.

11. The method of claim 10, wherein the at least five factors comprise four thermal factors about the animal and one thermal factor about the animal's environment.

12. The method of any one of claim 9, wherein the method comprises
   combining the behavioural information and the thermal information to generate the thermal profile value, the thermal profile value being indicative of at least one biological state in an animal.

13. The method of claim 9, wherein the behavioural information may comprise a kinematic expression or anatomical aspect about the animal.

14. The method of claim 9, wherein the at least one biological state may be selected from the group consisting of a disease state, metabolic efficiency, and a reproductive state.

* * * * *